US012692479B2

(12) United States Patent
Ebrahimkhani et al.

(10) Patent No.: US 12,692,479 B2
(45) Date of Patent: Jul. 28, 2026

(54) GENETICALLY ENGINEERED HUMAN FETAL LIVER NICHE AS PLATFORM FOR BIOMANUFACTURING OF HEMATOPOIETIC STEM CELLS

(71) Applicant: Arizona Board of Regents on behalf of Arizona State University, Scottsdale, AZ (US)

(72) Inventors: Mo Reza Ebrahimkhani, Scottsdale, AZ (US); Jeremy Velazquez, Pittsburgh, PA (US); Samira Kiani, Scottsdale, AZ (US); Ryan Patrick LeGraw, Pittsburgh, PA (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 1123 days.

(21) Appl. No.: 17/634,766

(22) PCT Filed: Aug. 12, 2020

(86) PCT No.: PCT/US2020/045926
§ 371 (c)(1),
(2) Date: Feb. 11, 2022

(87) PCT Pub. No.: WO2021/030433
PCT Pub. Date: Feb. 18, 2021

(65) Prior Publication Data
US 2022/0282219 A1 Sep. 8, 2022

Related U.S. Application Data

(60) Provisional application No. 62/885,651, filed on Aug. 12, 2019.

(51) Int. Cl.
| | |
|---|---|
| *A61K 35/28* | (2015.01) |
| *C07K 14/47* | (2006.01) |
| *C12N 5/071* | (2010.01) |
| *C12N 5/0789* | (2010.01) |

(52) U.S. Cl.
CPC ............ *C12N 5/0647* (2013.01); *A61K 35/28* (2013.01); *C07K 14/4705* (2013.01); *C12N 5/0671* (2013.01); *C12N 2500/98* (2013.01); *C12N 2501/125* (2013.01); *C12N 2501/145* (2013.01); *C12N 2501/26* (2013.01); *C12N 2502/13* (2013.01); *C12N 2502/14* (2013.01); *C12N 2502/28* (2013.01); *C12N 2506/45* (2013.01); *C12N 2513/00* (2013.01); *C12N 2531/00* (2013.01)

(58) Field of Classification Search
None
See application file for complete search history.

(56) References Cited

U.S. PATENT DOCUMENTS

| | | | |
|---|---|---|---|
| 10,435,710 | B2 | 10/2019 | Guye et al. |
| 2012/0003195 | A1 | 1/2012 | Mitrani |
| 2016/0002602 | A1 | 1/2016 | Almeida-Porada et al. |
| 2018/0258400 | A1 | 9/2018 | Ng et al. |

FOREIGN PATENT DOCUMENTS

WO        2019237124        12/2019

OTHER PUBLICATIONS

Flores-Guzman, P., Fernandez-Sanchez, V., Valencia-Plata, I., Arriaga-Pizano, L., Alarcon-Santos, G. and Mayani, H. (2013) Comparative in vitro analysis of different hematopoietic cell populations from human cord blood: in search of the best option for clinically oriented ex vivo cell expansion. Trans. (Year: 2013).*
Chou S, Flygare J, Lodish HF. Fetal hepatic progenitors support long-term expansion of hematopoietic stem cells. Exp Hematol. May 2013;41(5):479-490.e4. doi: 10.1016/j.exphem.2013.02.003. Epub Feb. 13, 2013. PMID: 23415675; PMCID: PMC3701434. (Year: 2013).*
Guye, P., Ebrahimkhani, M., Kipniss, N. et al. Genetically engineering self-organization of human pluripotent stem cells into a liver bud-like tissue using Gata6. Nat Commun 7, 10243 (2016). https://doi.org/10.1038/ncomms10243 (Year: 2016).*
Park JH, Pérez RA, Jin GZ, Choi SJ, Kim HW, Wall IB. Microcarriers designed for cell culture and tissue engineering of bone. Tissue Eng Part B Rev. Apr. 2013; 19(2):172-90. doi: 10.1089/ten.TEB. 2012.0432. Epub Jan. 17, 2013. PMID: 23126371. (Year: 2013).*
Armulik, A., Genove, G. & Betsholtz, C. Pericytes: developmental, physiological, and pathological perspectives, problems, and promises. Dev Cell 21, 193-215 (2011).
Chavez, A., et al. Highly efficient Cas9-mediated transcriptional programming. Nat Methods 12, 326-328 (2015).
Chen, Q., et al. Human fetal hepatic progenitor cells are distinct from, but closely related to, hematopoietic stem/progenitor cells. Stem Cells 31, 1160-1169 (2013).
Dahlberg, A., Delaney, C. & Bernstein, I.D. Ex vivo expansion of human hematopoietic stem and progenitor cells. Blood 117, 6083-6090 (2011).
Delaney, C., Varnum-Finney, B., Aoyama, K., Brashem-Stein, C. & Bernstein, I.D. Dose-dependent effects of the Notch ligand Delta1 on ex vivo differentiation and in vivo marrow repopulating ability of cord blood cells. Blood 106, 2693-2699 (2005).
Gao et al., "Fetal liver: an ideal niche for hematopoietic stem cell expansion," Science China Life Sciences, Jun. 15, 2018, vol. 61, No. 8, pp. 885-892.

(Continued)

*Primary Examiner* — Anna Skibinsky
*Assistant Examiner* — Catherine L McCormick
(74) *Attorney, Agent, or Firm* — Quarles & Brady LLP

(57) ABSTRACT

The present disclosure relates to methods for expanding populations of hematopoietic stem cells (HSCs) using a genetically engineered human fetal liver niche and compositions of purified ex vivo expanded HSCs. Also provided herein are methods of using such expanded HSC cell populations for clinical applications including allogeneic hematopoietic stem cell transplantation and for drug discovery and modeling human liver development.

15 Claims, 31 Drawing Sheets

(56)    References Cited

OTHER PUBLICATIONS

Guye, P., et al. Genetically engineering self-organization of human pluripotent stem cells into a liver bud-like tissue using Gata6. Nature Communications, Jan. 6, 2016, vol. 7, Art. No. 10243, pp. 1-12.

International Search Report and Written Opinion for corresponding PCT Application No. PCT/US2020/045926, mailed Nov. 6, 2020.

Khan et al., "Fetal liver hematopoietic stem cell niches associate with portal vessels," Science 2016, 351 (6269):176-180.

Kiani, S., et al. Cas9 gRNA engineering for genome editing, activation and repression. Nat Methods 12, 1051-1054 (2015).

Kiani, S., et al. CRISPR transcriptional repression devices and layered circuits in mammalian cells. Nat Methods 11, 723-726 (2014).

Kowalczyk, M., Waldron, K., Kresnowati, P. & Danquah, M.K. Process challenges relating to hematopoietic stem cell cultivation in bioreactors. J Ind Microbiol Biotechnol 38, 761-767 (2011).

Kunisaki, Y. & Frenette, P.S. The secrets of the bone marrow niche: Enigmatic niche brings challenge for HSC expansion. Nat Med 18, 864-865 (2012).

Liu, Y., Liu, T., Fan, X., Ma, X. & Cui, Z. Ex vivo expansion of hematopoietic stem cells derived from umbilical cord blood in rotating wall vessel. J Biotechnol 124, 592-601 (2006).

Lu et al., "Long-Term Safety and Function of RPE from Human Embryonic Stem Cells in Preclinical Models of Macular Degeneration," Stem Cells 2009;27:2126-2135.

Mendelson, A. & Frenette, P.S. Hematopoietic stem cell niche maintenance during homeostasis and regeneration. Nat Med 20, 833-846 (2014).

Miller, C.L. & Eaves, C.J. Expansion in vitro of adult murine hematopoietic stem cells with transplantable lympho-myeloid reconstituting ability. Proc Natl Acad Sci U S A 94, 13648-13653 (1997).

Ng et al., "Human iPS derived progenitors bioengineered into liver organoids using an inverted colloidal crystal poly (ethylene glycol) scaffold," Biomaterials, Nov. 30, 2018, vol. 182, pp. 299-311.

Reya, T., et al. A role for Wnt signalling in self-renewal of haematopoietic stem cells. Nature 423, 409-414 (2003).

Thomson et al., "Embryonic Stem Cell Lines Derived from Human Blastocysts," Science 282:1145-1147 (1998).

Velazquez and LeGraw et al., Synthetic Maturation of Multilineage Human Liver Organoids via Genetically Guided Engineering (2020) BioRxiv, doi: 10.1101/2020.05.10.087445.

Vo, L.T. & Daley, G.Q. De novo generation of HSCs from somatic and pluripotent stem cell sources. Blood 125, 2641-2648 (2015).

Walasek, M.A., van Os, R. & de Haan, G. Hematopoietic stem cell expansion: challenges and opportunities. Ann N Y Acad Sci 1266, 138-150 (2012).

Willert, K., et al. Wnt proteins are lipid-modified and can act as stem cell growth factors. Nature 423, 448-452 (2003).

Yu et al., "Induced Pluripotent Stem Cell Lines Derived from Human Somatic Cells," sciencexpress.org / Nov. 20, 2007 / 10.1126/science.1151526.

Fujikura et al., 2002 "Differentiation of embryonic stem cells is induced by GATA factors" Genes Dev;16(7):784-9. doi: 10.1101/gad.968802.

Li et al., 2004. "Distinct GATA6- and laminin-dependent mechanisms regulate endodermal and ectodermal embryonic stem cell fates" Nov. 2004;131(21):5277-86. doi: 10.1242/dev01415. Epub Sep. 29, 2004.

Morrisey et al., 1996. "GATA-6: a zinc finger transcription factor that is expressed in multiple cell lineages derived from lateral mesoderm" Dev Biol. 177(1):309-22. doi: 10.1006/dbio.1996.0165.

* cited by examiner

| Name | P-value | score |
|------|---------|-------|
| 1 Liver | $1.647 \times 10^{-19}$ | 79.09 |
| 2 Fetal Liver | $1.304 \times 10^{-12}$ | 36.53 |
| 3 Placenta | 0.00004424 | 14.62 |
| 4 Kidney | 0.00002862 | 13.98 |
| 5 Intestine | 0.02335 | 5.63 |
| 6 Lung | 0.1658 | 2.67 |
| 7 Adipocyte | 0.1658 | 2.06 |

Mesenchyme (septum transversum)

Hepatoblasts

Primitive endothelial cells

Engineering Human liver bud *in vitro*

FIG. 5
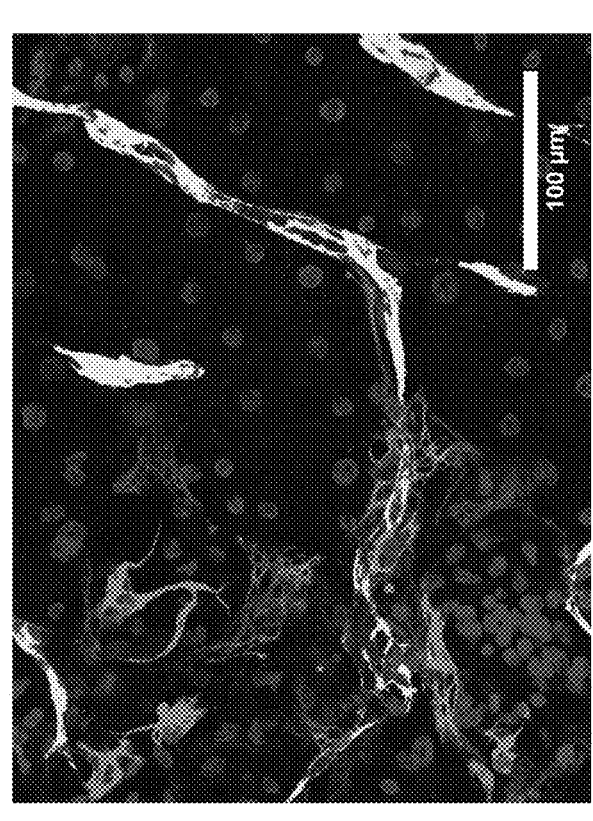
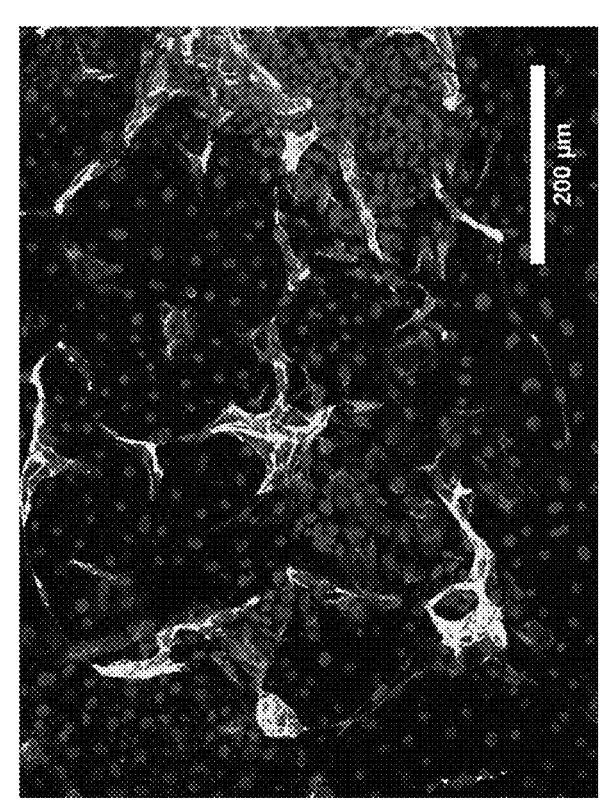

FIG. 6
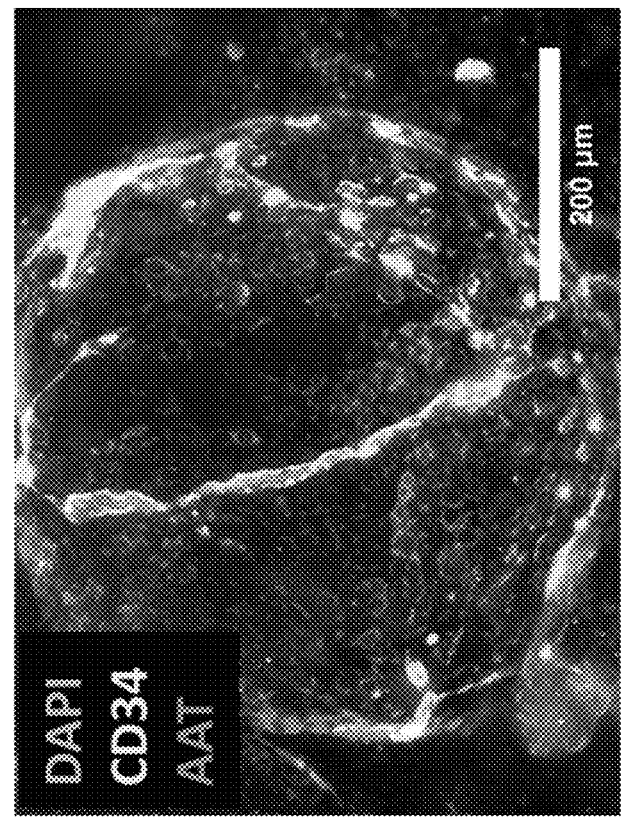
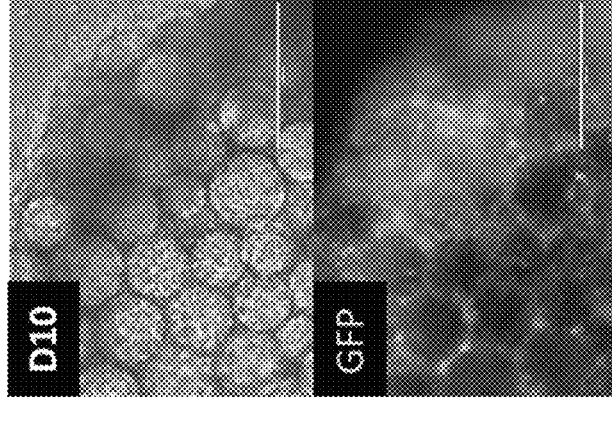
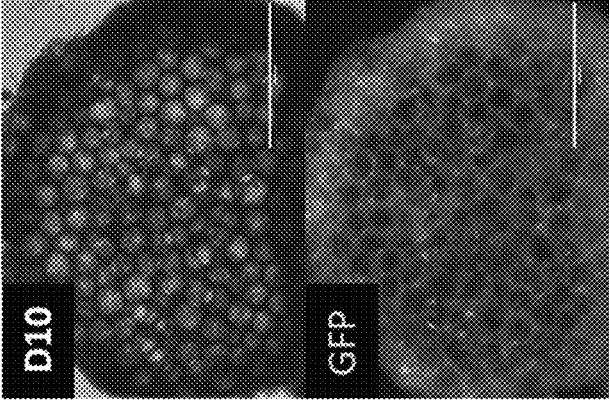

1: Hepatocyte-like cells 1
2: Cholangiocyte-like cells
3: Hepatocyte-like cells 2
4: Stellate-like cells
5: Endothelial-like cells

FIG. 11A

Blood Cell Markers

Niche Markers

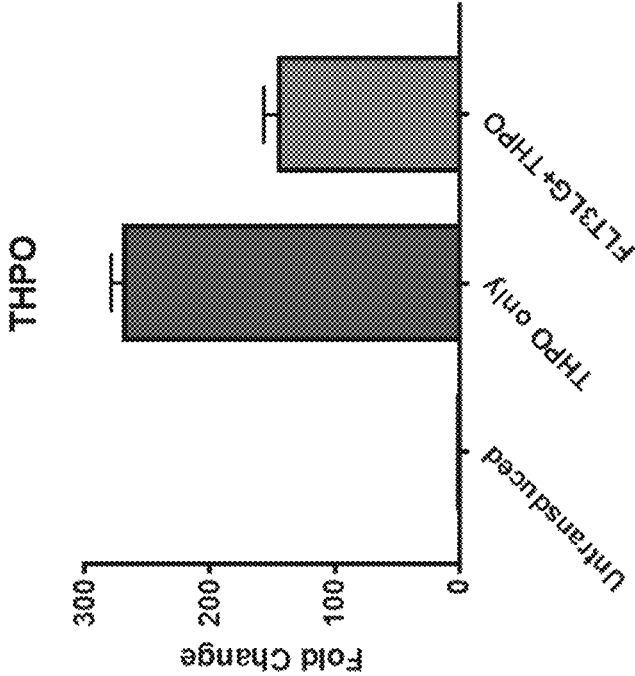
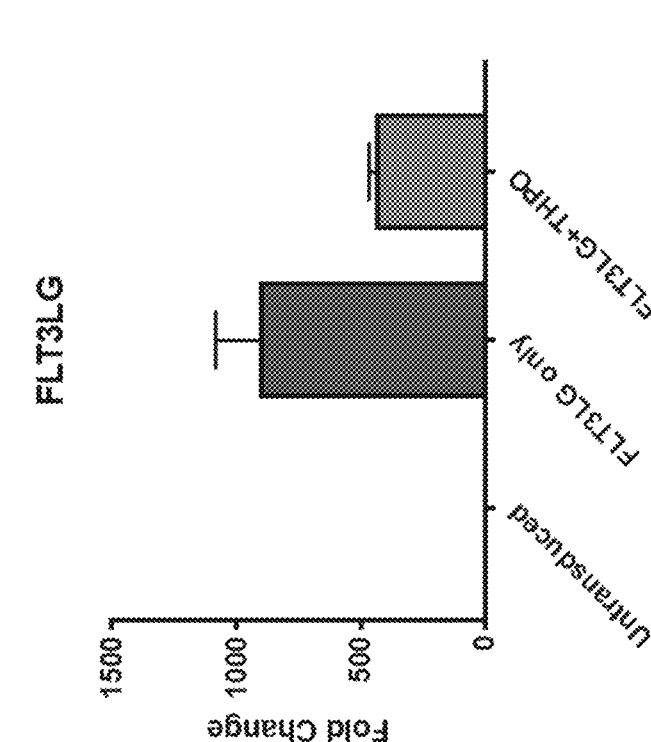
FIG. 12

FIG. 15
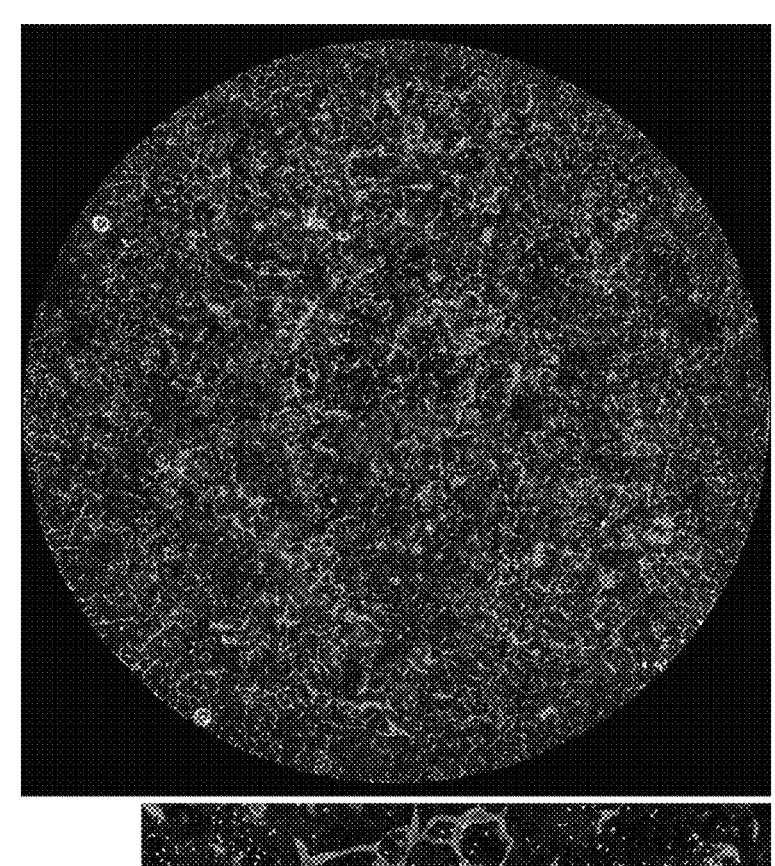
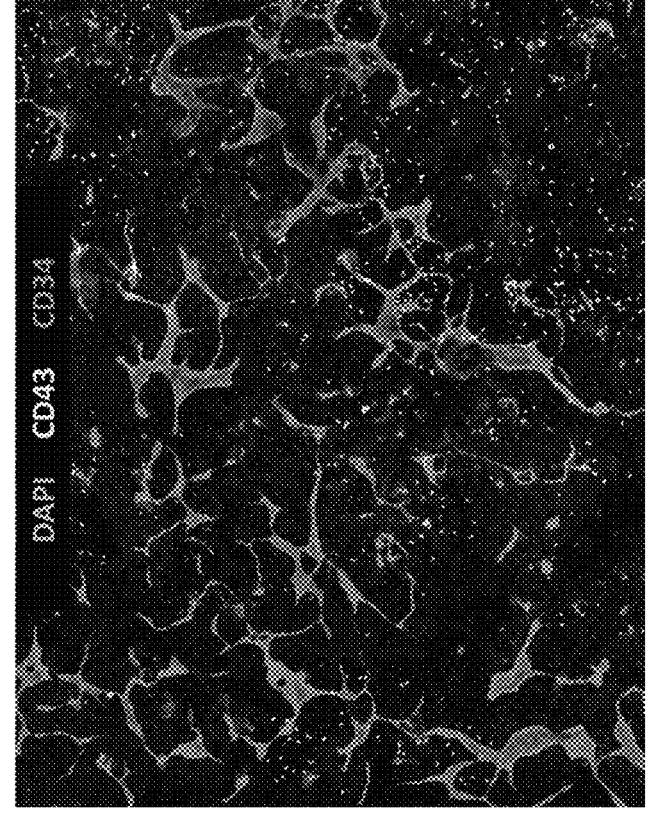

FIG. 18

Total Cell Counts

| Condition Name | Identity |
|---|---|
| Uncoated | CD34+ cord blood cells cultured on uncoated plates |
| MSC | CD34+ cord blood cells cultured on MSCs |
| FLIN | CD34+ cord blood cells cultured on FLIN |

FLIN

Uncoated

FLIN

FIG. 23

| | Material | Description | Cost |
|---|---|---|---|
| Conventional | SCF | Minimum required growth factor | $2 ml (~100ng) |
| | Flt3-L | Minimum required growth factor | $3 ml (~100ng) |
| | TPO | Minimum required growth factor | $1.3 ml (~100ng) |
| | Base medium | IMDM and TIB %20 (Cell Stem Cell 2012;10(2):218-29.) | $0.6ml |
| | TOTAL $$ ml/day | | $6.9ml/day |
| FLIN/DESLIN | Dox | Small molecule | $0.04/ml |
| | mTeSR Media | Commercially available (5 days) | 0.5ml (used in first 5 days) |
| | APEL | Made in house (Ref) (10 days) | 0.18ml (following 15 days) |
| | TOTAL $$ ml/day | *based on average media for 20 days | ~$0.25ml/day |

GENETICALLY ENGINEERED HUMAN FETAL LIVER NICHE AS PLATFORM FOR BIOMANUFACTURING OF HEMATOPOIETIC STEM CELLS

CROSS-REFERENCE TO RELATED APPLICATIONS

This application is a national stage application filed under 35 U.S.C. § 371 of International Application No. PCT/US2020/045926, filed Aug. 12, 2020, which claims the benefit of U.S. Provisional Application No. 62/885,651, filed Aug. 12, 2019 which is incorporated herein by reference in its entirety.

STATEMENT REGARDING FEDERALLY FUNDED RESEARCH

This invention was made with government support under grant number R01 HL141805 awarded by the National Institutes of Health. The government has certain rights in the invention.

BACKGROUND

Despite significant advances in our understanding of hematopoietic stem cell (HSC) transplantation and biology, the widespread clinical application of promising HSC therapy for hematologic diseases, immunodeficiency such as HIV/AIDS, and cancer is still rendered insufficient due to the paucity of optimally human leukocyte antigen (HLA)-matched donor HSCs. Umbilical cord blood, adult bone marrow, and peripheral blood are common sources for HSC isolation and transplantation. However, the number of HSCs recovered following isolations is generally too low as HSCs are only present in small concentrations in these pools. Therefore, strategies have been employed to enrich HSCs, such as selection based on surface antigen CD34, a marker associated with HSCs. In all these cases, low in vivo concentrations demand large volumes of donor tissues. To date, expansion of HSCs ex vivo for enhanced in vivo engraftment in patients have been clinically ineffective. In addition, as most techniques for ex vivo expansion of HSCs and progenitor cells require the addition of combinations of hematopoietic growth factors and synthetic small molecular weight compounds, large-scale production of HSCs is challenged by the cost associated with these factors and compounds. In addition, the need to manually and sequentially treat the culture with required growth factors further complicates the batch-to-batch reproducibility of large-scale production. Accordingly, there remains a need in the art for methods of maintaining and expanding patient-derived HSCs ex vivo.

SUMMARY OF THE DISCLOSURE

In a first aspect, provided herein is a method for ex vivo expansion of hematopoietic stem cells (HSCs). The method can comprise or consist essentially of (a) contacting a cell population comprising human hematopoietic stem cells (HSCs) to a synthetic fetal liver organoid comprising mesenchymal-like cells, CD34-expressing (CD34$^+$) endothelial-like cells, desmin-expressing (DES$^+$) stellate-like cells, and CEBPα$^+$ hepatocyte-like cells; and (b) culturing the contacted organoid under conditions that promote HSC proliferation for about 3 to about 10 days, whereby an expanded population comprising CD34+ human HSCs is obtained.

The expanded population can comprise at least 3-fold more CD34+ HSCs than the cell population of step (a). The method can further comprise obtaining the cell population of step (a) from a human subject. The cell population comprising HSCs can be derived from umbilical cord blood or bone marrow. The synthetic fetal liver organoid can constitute a coating on a solid carrier. The carrier can be a particulate support. The method can further comprise administering the expanded population of CD34+ human HSCs to a subject from whom the original cell population comprising HSCs is obtained. The contacted organoid can be cultured in a medium selected from IMDM medium and APEL medium. The culture medium can be supplemented with one or more of Stem Cell Factor (SCF), FMS-like Tyrosine Kinase 3 Ligand (FLT3L), and Thrombopoietin (TPO). At least a portion of cells of the synthetic fetal liver organoid can be genetically modified to express one or more of Stem Cell Factor (SCF), FMS-like Tyrosine Kinase 3 Ligand (FLT3L), and Thrombopoietin (TPO). The synthetic fetal liver organoid can be obtained by: (i) introducing into human pluripotent stem cells (hPSCs) one or more vectors comprising an inducible transgene encoding GATA-binding protein 6 (GATA6); (ii) inducing expression of the GATA6 transgene in the hPSCs; (iii) culturing the induced hPSCs in the presence of a pluripotency supporting medium for about 5 days, whereby a cell population comprising at least 70% CXCR4$^+$ cells is obtained; and (iv) culturing the cell population of step (iii) in a basal cell culture medium for about 10 days, whereby a synthetic, vascularized fetal liver organoid comprising CD34$^+$ endothelial-like cells, NES$^+$ mesenchymal stem cell-like cells, DES$^+$ stellate-like cells, and CEBPα$^+$ hepatocyte-like cells is obtained. The human pluripotent stem cells can be human embryonic stem cells or human induced pluripotent stem cells. The synthetic fetal liver organoid can exhibit one or more properties selected from (i) an interconnected vasculature; (ii) differentiated cells within the mature liver organoid mutually contact each other in three dimensions; and (iii) more than one layer of cells.

In another aspect, provided herein is a population of human HSCs expanded ex vivo according to a method of this disclosure.

In a further aspect, provided herein is a pharmaceutical composition comprising (a) a population of human HSCs expanded ex vivo according to a method of this disclosure and (b) a pharmaceutically acceptable carrier.

In another aspect, provided herein is a method of treating hematopoietic system deficiency in a human subject in need thereof. The method can comprise or consist essentially of the step of administering a therapeutically effective amount of a pharmaceutical composition of this disclosure to the human subject, whereby the administering treats the hematopoietic system deficiency in the human subject. The hematopoietic system deficiency can be anemia, a myelodysplasia syndrome, a complication of chemotherapy, a complication of bone marrow donation, a complication of radiation therapy, leukemia, or lymphoma. The HSCs can be autologous or allogeneic to the subject.

BRIEF DESCRIPTION OF THE DRAWINGS

FIG. 5 demonstrates that Desmin-expressing pericyte-like cells localize with the CD31-expressing endothelium.

FIG. 6 demonstrates microcarrier beads coated with a single cell suspension obtained from FLIN cultures. On day 14 of microcarrier bead culture, staining reveals that the microcarrier bead format supports CD34+ endothelial cells and AAT+ hepatic cells.

FIG. 11A is a set of heatmaps showing gene expression levels of select fetal liver hematopoietic related markers relevant for HSC cultures. Conditions include CD34+, CD34−CD146+, and CD34−/CD146− double negative cells isolated using magnetic beads (Miltenyi Biotech) from FLIN. Low MOI DesLO (lDesLO), and high MOI DesLO (hDesLO) shows FLIN that is additionally engineered via over expression of ATF5, PROX1 and CRISPR-based activation of CYP3A4 to ignite maturation of fetal liver. These populations represent cell populations found in the fetal liver. The data shows presence of wide variety of signals important for HSC homeostasis.

FIG. 12 presents qPCR data demonstrating upregulation of the hematopoietic cytokines FLT3LG and THPO following transduction of the FLIN with lentiviral expression vectors for FLT3LG only, THPO only, or FLT3LG and THPO together.

FIG. 15 demonstrates that human CD34+ cord blood-derived HSCs co-cultured for 7 days on FLIN show expansion of hematopoietic progenitor cells marked by CD43 expression (expressed on hematopoietic cells) among the prominent CD34+ vascular beds.

FIG. 18 is a graph depicting daily total cell counts for CD34+ cells seeded into uncoated plates, into MSC co-cultures, and FLIN co-cultures, demonstrating that the greatest increase in total cell numbers occurred in FLIN co-cultures.

FIG. 23 is a table comparing production costs for FLIN-based HSC expansion to costs for cytokine-based HSCs expansion.

DETAILED DESCRIPTION OF THE DISCLOSURE

Figures 1A, 1B:
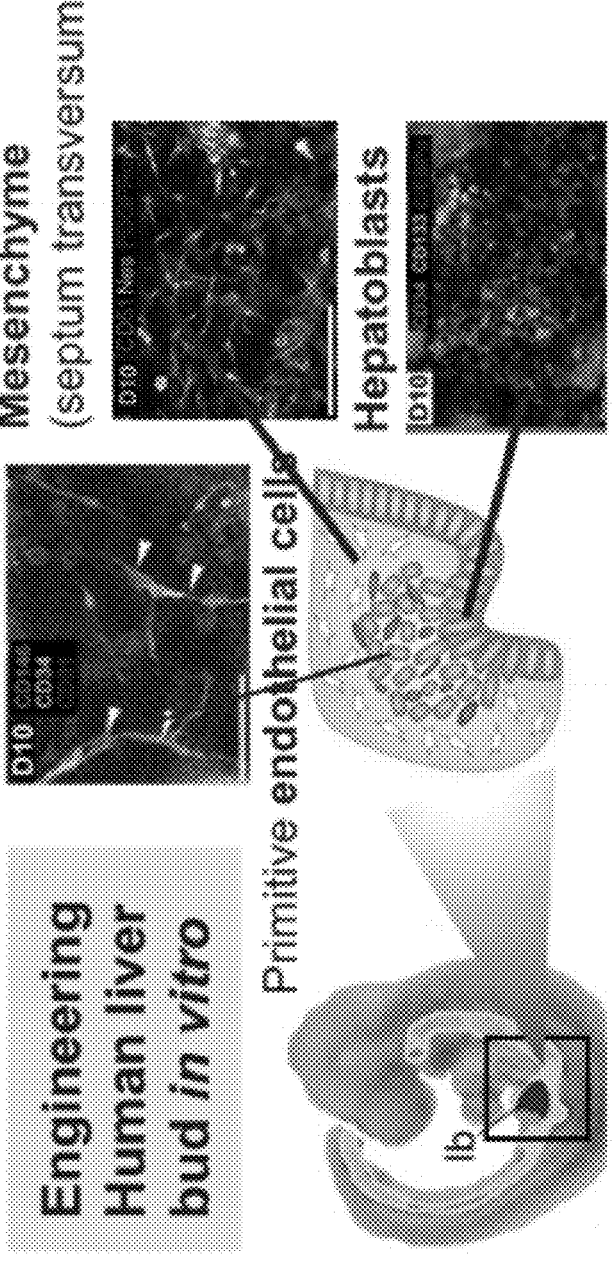
FIGS. 1A-1B demonstrate that human fetal liver niche (FLIN) tissue at day 15 recapitulates the complexity of a human fetal liver in terms of cell types and genetic signatures. (A) Table presents whole transcriptomic analyses showing high degrees of similarity between FLIN and human fetal liver. (B) Schematic shows engineered FLIN encompasses tissues and cells from different germ layers similar to a fetal liver.
Figure 2:
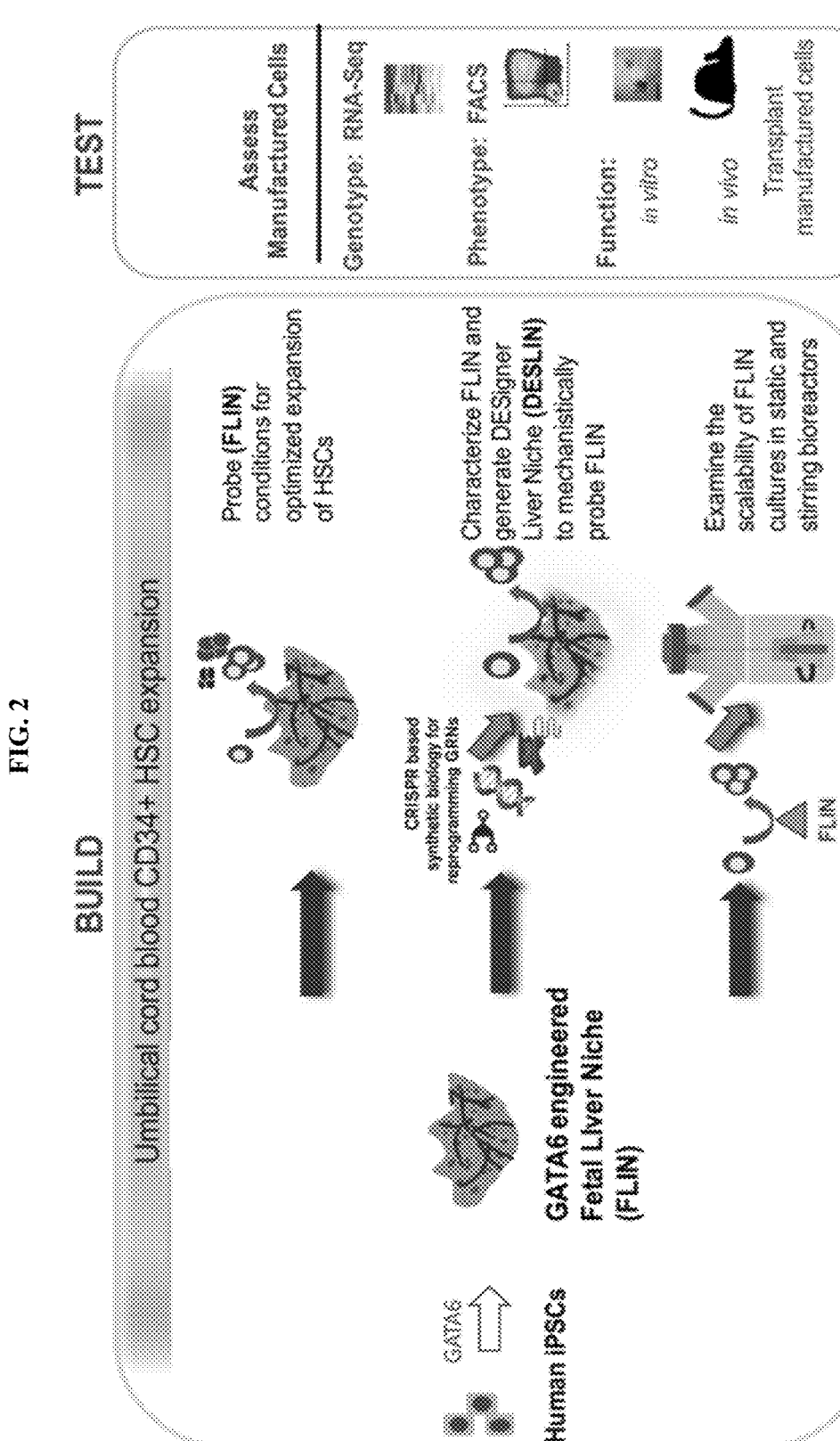
FIG. 2 illustrates an exemplary protocol for developing a human HSC expansion platform.

All publications, including but not limited to patents and patent applications, cited in this specification are herein incorporated by reference as though set forth in their entirety in the present application.

Stem cell self-renewal and differentiation are regulated through intricate crosstalk with neighboring cell types, which secrete and organize a multifaceted milieu of signaling cues (stem cell niche). Removing stem cells from their native environment can disrupt this homeostasis. HSCs experience limited self-renewal in the bone marrow niche (BM) and are typically quiescent. In contrast, in fetal liver, HSCs undergo marked expansion and become highly proliferative, which suggests that the fetal liver niche provides a unique microenvironment for HSCs (Khan et al., *Science* 2016, 351(6269):176-180). However, access to viable human fetal liver is challenging due to ethical constraints. By genetically engineering human pluripotent stem cells (hPSCs), the inventors developed a fetal liver tissue with hematopoietic niche capacity. The fetal liver niche is uniquely positioned to support HSC expansion.

The methods and compositions provided herein are based on the inventors' development of GATA6-engineered vascularized human fetal liver having the capacity to act as a niche to support hematopoiesis ex vivo. Further, the inventors determined that the GATA6-engineered vascularized human fetal liver niche (FLIN) tissue provides a useful platform to support expansion and differentiation of patient HSCs ex vivo relevant for scalable biomanufacturing of HSCs. By integrating synthetic biology and clustered regularly interspaced short palindromic repeats (CRISPR) technologies, the platform provides a customizable FLIN for enhanced HSC expansion.

Accordingly, the embodiments described herein encompass methods of expanding and differentiating HSCs using synthetic fetal liver tissue organoids to produce human HSCs on a commercial scale. Expanded populations of human HSCs prepared according to the methods of this disclosure can be used for cell-based regenerative therapies and other clinical applications.

Methods of Preparing Ex Vivo Expanded HSC Populations

In a first aspect, provided herein is a method for ex vivo expansion of hematopoietic HSCs. Preferably, the method comprises contacting a cell population comprising human hematopoietic stem cells (HSCs) to a synthetic vascularized human fetal liver niche (FLIN), referred to herein as a synthetic fetal liver organoid, and culturing the contacted organoid under conditions that promote HSC proliferation for a length of time between about 3 to about 10 days (e.g., about 3, 4, 5, 6, 7, 8, 9, 10 days, inclusive), whereby an expanded population comprising human CD34+ HSCs is obtained. Preferably, the contacted organoid is cultured for about 4 days to about 7 days (e.g., about 4, 5, 6, 7 days, inclusive). In some cases, the culture conditions comprise chemically defined, serum-free, and/or xeno-free culture conditions.

As used herein, the term "hematopoietic stem cell" refers to an immature progenitor cell of the hematopoietic lineage. Upon differentiation, HSCs can give rise to all types of blood cells, including white blood cells, red blood cells, and platelets. Hematopoietic stem cells are found in the peripheral blood, the bone marrow, and umbilical cord blood. Accordingly, a cell population comprising human HSCs is a plurality of human cells where at least a portion of the plurality are human HSCs. Human HSCs in their undifferentiated state are characterized in vitro and in vivo by expression of cell surface marker CD34+.

As used herein, the term "synthetic fetal liver organoid" refers to an in vitro-derived tissue construct that comprises human endodermal and mesodermal layers, hepatoblasts, endothelial, biliary and stellate (-like) cells, and generally recapitulates the structure, composition, and complexity of liver tissue in the developing human embryo. In some cases, the synthetic fetal liver organoid is a GATA6-engineered vascularized human fetal liver niche prepared using human pluripotent stem cells. Accordingly, synthetic fetal liver organoids as demonstrated herein provide a unique, customizable niche for ex vivo expansion of HSCs.

As used herein, the term "expand" refers to increasing in number, as in an increase in the number of cells (e.g., HSCs). Preferably, the cells that are expanded ex vivo increase in number relative to the number originally present in the culture. In some cases, the cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

In some cases, HSCs expanded according to the methods described herein are expanded at least 2-fold relative to the number of CD34$^+$ HSCs originally present in the cell population prior to contacting to the synthetic fetal liver niche. HSCs can be expanded according to the methods provided herein by approximately 2 fold, 3 fold, 4 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, 100 fold, 200 fold, 300 fold, 400 fold, 500 fold or greater. In one embodiment, HSCs are expanded ex vivo in the range of about 2 fold to about 10 fold, or more.

Hematopoietic stem cells for use according to the methods of this disclosure can be obtained according to methods known in the art, including, for example, by detecting expression of specific cell surface proteins or receptors, cell surface protein markers, or other markers. In some cases, human HSCs can be isolated from a population of cells obtained from hematopoietic tissue samples such as bone marrow cavities, umbilical cord blood, placenta, and (generally in low numbers) in circulating blood and in spleen tissue. In other cases, HSCs are obtained by expansion and differentiation of hematopoietic progenitors. Preferably, isolated HSC cell populations are substantially pure such that at least 60% (or at least 65%, 70%, 75%, 80%, 85%, 90%, 95%, or 99%) of the cells are CD34$^+$ HSCs. The terms "pure," "purified" or "enriched" cell populations are used interchangeably herein, and refer to cell populations, in vitro or ex vivo, that contain a higher proportion of a specified cell type or cells having a specified characteristic than are found in vivo (e.g., in a tissue).

In some cases, it may be advantageous to genetically modify ex vivo expanded HSCs obtained according to the methods provided herein. For example, it can be advantageous in some instances to obtain genetically-modified HSCs that produce recombinant cell products, growth factors, hormones, peptides or proteins for a continuous amount of time or as needed when biologically, chemically, or thermally signaled due to the conditions present in culture. In other cases, it can be advantageous to genetically modify HSCs obtained according to the methods herein in order to introduce a mutation (e.g., insertion, deletion, SNP). In some cases, genetic modifications are produced using a form of gene editing. The term "gene editing" and its grammatical equivalents as used herein can refer to genetic engineering in which one or more nucleotides are inserted, replaced, or removed from a genome. For example, gene editing can be performed using a nuclease (e.g., a natural-existing nuclease or an artificially engineered nuclease). In some cases, gene editing is performed using a CRISPR/Cas system. In some cases, the protein expression of one or more endogenous genes is reduced using a CRISPR/Cas system. In other cases, a CRISPR/Cas system can be used to perform site specific insertion. For example, a nick on an insertion site in the genome can be made by CRISPR/Cas to facilitate the insertion of a transgene at the insertion site. Other methods of making genetic modifications suitable for use according to the methods provided herein include but are not limited to somatic cell nuclear transfer (SCNT) and introduction of a transgene. As used herein, the term "transgene" refers to a gene or genetic material that can be transferred into an organism or a cell thereof. Procedures for obtaining recombinant or genetically modified cells are generally known in the art, and are described in Sambrook et al, *Molecular*

*Cloning, A Laboratory Manual*, Cold Spring Harbor Press, Cold Spring Harbor, N.Y. (1989), incorporated herein by reference.

In some cases, it will be advantageous to employ gene editing techniques to modify gene regulatory networks to modulate HSC proliferation when contacted to genetically modified synthetic fetal liver organoids. For example, CRISPR repression circuits to transcriptionally repress expression of particular signaling molecules that act as negative regulatory factor for hematopoiesis in human fetal liver. DLK1 is non-canonical notch ligand. DLK1+ hepatoblasts are known to play key roles to promote expansion of HSCs. Paradoxically, expression of DLK1 inhibits proliferation of HSCs, suggesting that DLK1 may act as a negative regulatory factor for hematopoiesis in the human fetal liver. Fetal liver niches prepared as described herein express high levels of DLK1. Accordingly, in some cases CRISPR repression circuits can be used to transcriptionally repress DLK1 expression prior to or during culture of HSCs on the fetal liver niche. Likewise, CRISPR-based repression circuits can be used to modulate expression of other molecules known to be inhibitors of HSC proliferation.

In some cases, the HSCs to be contacted to or in contact with the synthetic fetal liver organoid are cultured in the presence of one or more transcription factors or cytokines that are known to enhanced hematopoiesis. Exemplary factors include, without limitation, Stem Cell Factor (SCF), FMS-like Tyrosine Kinase 3 Ligand (FLT3L), and Thrombopoietin (TPO). In other cases, CRISPR-mediated synthetic biology is used to build spatiotemporally regulated synthetic CRISPR-based genetic circuits (e.g., CRISPR activators) to activate the expression of core developmentally conserved pathways (e.g., wingless-type (Wnt), Notch, Sonic hedgehog (Shh), and fibroblast growth factor (FGF) signaling) within the synthetic fetal liver organoid to further enhance hematopoietic expansion capacity (SCF, FLT3L, and TPO). In such cases, the genetically enhanced fetal liver niche described herein can act as a universal, customizable expansion platform for enhanced hematopoiesis. It is a programmable niche to self-generate desired cytokines, hence decreasing the cost.

In some cases, the HSC-contacted fetal liver organoid is cultured in the presence of human feeder cells. As demonstrated in the Examples, the feeder cells can be human mesenchymal stem cells (MSCs).

In some cases, the cell population comprising human HSCs and the synthetic fetal liver organoid are cultured in a medium that supports HSC proliferation. In some cases, the culture medium is IMDM or APEL medium. Other culture media appropriate for the methods of this disclosure include, without limitation, commercially available culture media such as STEM PRO, Xvivo (Lonza), E8 medium, and mTeSR1. In some cases, the culture medium comprises serum. In some cases, the culture medium is serum-free and, in some cases, chemically defined. The term "chemically defined culture medium" or "chemically defined medium," as used herein, means that the molecular identity, chemical structure, and quantity of each medium ingredient is definitively known. As used herein, the term "serum-free" refers to cell culture materials that are free of or substantially free of serum obtained from animal (e.g., fetal bovine) blood or serum replacement.

In some cases, HSCs are contacted to a synthetic fetal liver organoid in any appropriate cell culture substrate such as a tissue culture dish. In some cases, substrate is coated (partially or fully) with a defined extracellular matrix protein substrate or undefined extracellular matrix protein substrate such as Matrigel®.

In another aspect, ex vivo expanded HSCs obtained according to the disclosed methods may be further differentiated to various hematopoietic cell lineages which could be used in clinical applications.

In another aspect, provided herein are methods for large-scale production of HSCs. In some cases, the methods comprise contacting a cell population comprising HSCs to a synthetic fetal liver organoid produced on a solid micro-scale substrate such as a microcarrier bead or other solid particulate support. By coating a microcarrier bead or other support with a synthetic fetal liver organoid, micro-scale liver organoid is obtained. Microcarrier cultures accommodate higher cell densities than static cultures. Their high surface area-to-volume ratio makes them ideal for cell expansion with reduced cost. Microcarriers can be customized by attaching various synthetic peptides or extracellular matrix molecules, to accommodate the adhesion needs of diverse cell types. Referring to FIGS. 9A-9B, fetal liver niches (FLINs) prepared on microcarrier beads exhibit similar hematopoietic functions as compared to static culture on FLINs. Accordingly, production using micro-scale substrates such as microcarrier beads will dramatically increase the scale of HSC biomanufacturing while reducing the cost. Preferably, the micro-scale substrates are chemically defined and free of any components derived from a non-human animal (in other words, free of xenogeneic material or "xeno-free"). As used herein, the term "microcarrier" refers to a small, micro-scale, discrete particle for use in culturing cells and to which cells may attach in culture. Microcarriers may be of any suitable size. In some cases, microcarriers have a diameter between about 20 microns and 1000 microns. The size of the microcarrier can be readily controlled using microcarrier synthesis methods routinely used in the art. Microcarriers can have any suitable shape including, without limitation, spheres, ovals, rods, and cylinders, and may be porous or non-porous. As used herein, the term "non-porous" means having no pores or pores of an average size smaller than a cell with which the microcarrier is cultured, e.g., less than about 0.5-1 micrometers. Non-porous microspheres may be desirable when the microcarrier material is non-degradable. In other cases, for instance when the microcarriers are degradable e.g. if they include an enzymatically or otherwise degradable cross-linker, it may be advantageous to use porous microcarriers.

In some cases, the synthetic fetal liver organoid constitutes a coating on a solid carrier. To obtain a micro-scale organoid on a particulate support, a synthetic fetal liver organoid is dissociated into a single cell suspension using enzymatic dissociation. In some cases, the enzyme is Accutase.

Microcarriers appropriate for use in methods and compositions described herein include, without limitation, alginate-based microcarriers, dextran-based microcarriers, collagen-based microcarriers, polystyrene-based microcarriers, and the like. Microcarriers be made from a solid, a semi-solid, or a combination of a solid and a semi-solid, and can be used as a support or substrate such as support and substrate materials used in chemical and biological assays and syntheses. Non-limiting examples of these materials include cellulose, carboxymethyl cellulose, hydroxyethyl cellulose, agar, pore-glass, silica gel, polystyrene, brominated polystyrene, polyacrylic acid, polyacrylonitrile, poly-amide, polyacrolein, polybutadiene, polycaprolactone, poly-ester, polyethylene, polyethylene terephthalate, polydimethylsiloxane, polyisoprene, polyurethane, polyvi-nylacetate, polyvinylchloride, polyvinylpyridine, polyvinyl-benzylchloride, polyvinyltoluene, polyvinylidene chloride, polydivinylbenzene, polymethylmethacrylate, polylactide, polyglycolide, poly(lactide-co-glycolide), polyanhydride, polyorthoester, polyphosphazene, polyphosophaze, poly-sulfone, grafted copolymer such as polyethylene glycol/polystyrene, cross-linked dextrans, methylstyrene, polypro-pylene, acrylic polymer, carbon, graphite, polycarbonate, polypeptide, hydrogels, liposomes, proteinaceous polymer, titanium dioxide, latex, resin, lipid, ceramic, charcoal, metal, bentonite, kaolinite, rubber, polyacrylamide, latex, silicone, e.g., polydimethyldiphenyl siloxane, dimethylacrylamide, and the like or combinations thereof are acceptable as well. According to a particular embodiment, the microcarrier is itself a microparticle, i.e., a solid or semi-solid particle. In some cases, microcarriers may be used as-is. In other cases, microcarriers are coated with various compositions such as natural and synthetic polymeric coatings (such as vitronectin (e.g., native or recombinant vitronectin), Matrigel®, colla-gen, gelatin); metals including magnetic materials; and other coating materials routinely used in the art and suitable for use with human cells.

In some cases, a micro-scale organoid is cultured in a stirred suspension bioreactor for ex vivo expansion of the HSCs. In some cases, the methods comprise forming syn-thetic fetal liver organoids in flasks suitable for stirred-suspension culture (e.g., spinner-inside flasks). In some cases, the initial cell densities are between about $5 \times 10^4$ cells/ml to $50 \times 10^4$ cells/ml (e.g., about $5 \times 10^4$, $10 \times 10^4$, $15 \times 10^4$, $20 \times 10^4$, $25 \times 10^4$, $30 \times 10^4$, $35 \times 10^4$, $40 \times 10^4$, $45 \times 10^4$, or $50 \times 10^4$ cells/ml). The number of cells used for inocula-tion of the culture dictates largely the peak cell concentration that can be achieved and therefore the bioprocess demand in 02 and nutrients. FLIN development is driven by paracrine factors with concentration directly dependent on cell den-sity, particularly during induction of GATA6 expression. In static culture, GATA expression is induced for about 4, 5, or 6 days, but it will be understood that the duration of GATA induction will vary for spinning flask culture based on factors such as on the degree of agitation and the initial cell seeding concentration for each cell type. In some cases, HSCs are added to microcarrier FLIN cultures in the range of about $1 \times 10^4$, $5 \times 10^4$, or $10 \times 10^4$ HSCs/ml in 125-ml stirrer inside spinner flasks (SF). In some cases, the spinning agitation rate is in the range of about 40 rpm to about 60 rpm (e.g., 40 rpm, 50 rpm, 60 rpm).

In preferred embodiments, fetal liver organoids used for the methods described herein are prepared by directing in vitro differentiation of human progenitor cell types such as human pluripotent stem cells. Heterogeneous GATA6 expression can be genetically engineered in human pluripo-tent stem cells (hPSCs) through introduction of an inducible GATA6 cassette. For instance, an inducible cassette can be introduced using a Piggybac expression system. See, for example, WO2019237124, which is incorporated herein by reference in its entirety. When cultured in the presence of doxycycline (DOX) in a culture medium comprising bFGF and TGF-β (e.g., mTeSR culture medium) for about 5 days, the transfected cells differentiate into endodermal and meso-dermal progenitors. Following the five-day induction of GATA6 in a culture medium that supports pluripotency by addition of doxycycline, the progenitor cells co-differentiate and self-organize sequentially into vascularized fetal liver tissue in vitro without supplementation of any growth factor, thus forming a complex, fetal liver-like tissue organoid. See also Guye et al. (Genetically engineering self-organization of human pluripotent stem cells into a liver bud-like tissue using Gata6. *Nat Commun,* 7:10243 (2016)), which is incorporated herein by reference in its entirety. The fetal liver organoid contains hepatoblasts, Desmin+ stellate-like cells and CD34+ hemogenic endothelium. Within about two weeks, CD34+ endothelial tubes constrict and generate small spherical cells expressing CD45 or hemoglobin (HG) gamma, supportive of definitive fetal erythropoiesis. The resulting fetal liver organoid is a vascularized liver-like tissue comprising CCAAT/enhancer binding protein α (CEBPα)-expressing (CEBP-α⁺)/AAT⁺ hepatoblasts, CK19⁺/CK7⁺ cholangiocytes, CD34⁺ endothelium, and Desmin⁺ (DES⁺) stellate-like cells with hematopoiesis-like processes. Accordingly, GATA6-derived fetal liver organoids provide a multicellular human tissue that closely mimics key features of the fetal liver such as several subsets of stromal cells, endothelial cells, and vital cell signaling cues in a 3D configuration.

As used herein, the term "pluripotent stem cell" refers to a cell capable of continued self-renewal and of capable, under appropriate conditions, of differentiating into cells of all three germ layers. Examples of pluripotent stem cells (PSCs) include embryonic stem cells (ESCs) and induced pluripotent stem cells (iPSCs). As used herein, "embryonic stem cells" or "ESCs" mean a pluripotent cell or population of pluripotent cells derived from an inner cell mass of a blastocyst. See, e.g., Thomson et al., *Science* 282:1145-1147 (1998). These cells express Oct-4, SSEA-3, SSEA-4, TRA-1-60, and TRA-1-81, and appear in vitro as compact colonies having a high nucleus to cytoplasm ratio and prominent nucleolus. As used herein, the term "iPS cell" or "iPSC" refers to a pluripotent cell or population of pluripotent cells that may vary with respect to their differentiated somatic cell of origin, that may vary with respect to a specific set of potency-determining factors and that may vary with respect to culture conditions used to isolate them, but nonetheless are substantially genetically identical to their respective differentiated somatic cell of origin and display characteristics similar to higher potency cells, such as ESCs, as described herein. See, e.g., Yu et al., *Science* 318:1917-1920 (2007). iPSCs are substantially genetically identical to their respective differentiated somatic cell of origin, display characteristics similar to higher potency cells, such as ES cells, and cells are obtained by reprogramming non-pluripotent cells (e.g., multipotent cells, oligopotent cells, unipotent cells, and terminally differentiated cells) such as somatic cells. ESCs and iPSCs are available from various commercial suppliers.

In some cases, the synthetic fetal liver organoid is obtained by (i) introducing into human pluripotent stem cells (hPSCs) one or more vectors (e.g., expression vectors) comprising an inducible transgene encoding GATA-binding protein 6 (GATA6); (ii) inducing expression of the GATA6 transgene in the hPSCs; (iii) culturing the induced hPSCs in the presence of a pluripotency supporting medium for about 5 days, whereby a cell population comprising at least 70% CXCR4⁺ cells is obtained; and (iv) culturing the cell population of step (iii) in a basal cell culture medium for about 5 to about 10 days, whereby the cells self-organize into a synthetic fetal liver organoid that exhibits one or more properties selected from (1) an interconnected vasculature; (2) differentiated cells within the mature liver organoid mutually contact each other in three dimensions; and (3) more than one layer of cells.

In some cases, CD34+ cells of a synthetic fetal liver organoid are tagged with an intracellular dye such as intracellular fluorescent dye CFSE. In some cases, the fetal liver tissue contacted by the CD34+ cells expressing GATA6 are cultured in a three dimensional (3D) physical environment such as a rotating vessel. In some cases, the CD34-positive (CD34+) hematopoietic progenitor cells are obtained from human induced pluripotent stem cells derived by reprogramming somatic cells obtained from a human subject. Heterogeneous GATA6 expression can be genetically engineered in human pluripotent cells (human induced pluripotent stem cells or human embryonic stem cells) by introducing an inducible GATA6 cassette. In some cases, the GATA6 cassette is introduced by Piggybac or another method of delivering nucleic acids. Following a transient five-day induction of GATA6 in pluripotency medium by addition of doxycycline, the progenitor cells co-differentiated and self-organized sequentially into vascularized fetal liver tissue in vitro without supplementation of any growth factor. The developed fetal liver tissue contains hepatoblasts, Desmin+ stellate-like cells and CD34+ hemogenic endothelium. Around day 14, CD34+ endothelial tubes constrict and generate small spherical cells expressing CD45 or hemoglobin gamma, which is indicative of definitive fetal erythropoiesis.

Transcriptional analysis on day 5 of the culture protocol reveals the expression of factors associated with hemangioblast induction (e.g., VEGFA, CSF2, TIE2, and GATA1). Early progenitor commitment to hematopoietic development is also detected as early as day 8 through expression of CD43 (leukosialin) and TAL1 in CD34 expressing cells within hepatic endoderm layer. Further characterization of liver-like tissue showed cell types that are normally found in the developing liver bud and reported to act as key components of the hematopoietic niche such as Desmin+ stellate cells, nestin+ pericytes, mesenchymal precursors (mesenchymal-like cells). In vitro functional assays validated the presence of multipotent progenitors with an ability to undergo differentiation to erythroid and myeloid colonies.

In some cases, pluripotent stem cells (e.g., hiPSCs or hESCs) used to produce a fetal liver organoid are cultured in a chemically defined medium comprising a Rho Kinase (ROCK) inhibitor for about 1 day (about 24 hours) prior to start of a differentiation protocol as provided herein. In some cases, the chemically defined medium is mTeSR-1 and the ROCK inhibitor is Y-27632. ROCK inhibitors suitable for use herein include, but are not limited to, (S)-(+)-2-methyl-1-[(4-methyl-5-isoquinolinyl)sulfonyl]homopiperazine dihydrochloride (informal name: H-1152), 1-(5-isoquinolinesulfonyl)piperazine hydrochloride (informal name: HA-100), 1-(5-isoquinolinesulfonyl)-2-methylpiperazine (informal name: H-7), 1-(5-isoquinolinesulfonyl)-3-methylpiperazine (informal name: iso H-7), N-2-(methylamino)ethyl-5-isoquinoline-sulfonamide dihydrochloride (informal name: H-8), N-(2-aminoethyl)-5-isoquinolinesulphonamide dihydrochloride (informal name: H-9), N-[2-p-bromo-cinnamylamino)ethyl]-5-isoquinolinesulfonamide dihydrochloride (informal name: H-89), N-(2-guanidinoethyl)-5-isoquinolinesulfonamide hydrochloride (informal name: HA-1004), 1-(5-isoquinolinesulfonyl) homopiperazine dihydrochloride (informal name: HA-1077), (S)-(+)-2-Methyl-4-glycyl-1-(4-methylisoquinolinyl-5-sulfonyl)homopiperazine dihydrochloride (informal name: glycyl H-1152) and (+)-(R)-trans-4-(1-aminoethyl)-N-(4-pyridyl) cyclohexanecarboxamide dihydrochloride (informal name: Y-27632). Kinase inhibitors, such as ROCK inhibitors, are known to protect single cells and small aggregates of cells, including pluripotent stem cells. The kinase inhibitor can be provided at a concentration sufficiently high that the cells survive and remain attached to the surface. An inhibitor concentration between about 3 μM to about 10 μM can be suitable. At lower concentrations, or when no ROCK inhibitor is provided, undifferentiated cells typically detach, while differentiated cells remain attached to the defined surface.

Methods of Treatment

In another aspect, provided herein is a method for using an ex vivo expanded population of human HSCs obtained according to the methods of this disclosure for transplantation into a living animal. In particular, the methods comprise transplanting an ex vivo expanded population of human HSCs into a living animal (e.g., a mammal) for improved therapeutic applications. As described in the Examples, ex vivo expansion of HSCs can provide adequate numbers of HSCs for various therapeutic uses including hematopoietic stem cell transplantation (HSCT) (e.g., allogenic HSCT). As used herein, the term "transplant" and grammatical variations thereof refer to a biocompatible lattice or a donor tissue, organ, or cells to be implanted into or otherwise administered (e.g., injected into) to a host. An example of a transplant may include but is not limited to tissues, cell populations (e.g., expanded HSCs), bone marrow, and solid organs such as heart, pancreas, kidney, lung and liver, or portions there. A transplant can also refer to any material that is to be administered to a host. For example, a transplant can refer to a nucleic acid or a protein.

In some cases, provided herein is a method of treating a hematopoietic system deficiency in a human subject in need thereof. The method can comprise or consist essentially of administering to the human subject a therapeutically effective amount of an ex vivo expanded population of human HSCs obtained according to the methods of this disclosure and isolated for administration to a subject, whereby the administering treats the hematopoietic system deficiency.

As used herein, the term "treating" or "treatment" refers to administration of a composition comprising ex vivo expanded HSCs of this disclosure to a subject who has a disease or disorder (e.g., a hematopoietic system deficiency, bone marrow failure, anemia), with the purpose to cure, alleviate, relieve, remedy, delay the onset of, or ameliorate the disorder, the symptom of the disorder, the disease state secondary to the disorder, or the predisposition toward the disorder. In some cases, the subject will undergo a treatment that may affect hematopoiesis such as chemotherapy, radiation therapy, or bone marrow removal/extraction. In some cases, the subject has a malignant or non-malignant disease that impairs hematopoiesis or is associated with impaired hematopoiesis. Exemplary malignant diseases associated with impaired hematopoiesis include, without limitation, acute lymphocytic leukemia, acute myelocytic leukemia, juvenile chronic myelogenous leukemia, neuroblastoma, and myelodysplastic syndrome. Non-malignant diseases associated with impaired hematopoiesis include, without limitation, Fanconi anemia, idiopathic aplastic anemia, thalassemia, sickle cell anemia, amegakaryocytic thrombocytopenia, Kostman syndrome, Blackfan-Diamond syndrome, severe combined immunodeficiency, X-linked lymphocproliferative syndrome, Wiskoff Aldrich syndrome, Hurler syndrome, Hunter syndrome, Gunther disease, osteopetrosis, globoid cell leukodystrophy, adrenoleukodystrophy, and Lesch-Nyhan syndrome, neutropenia, and thromobocytopenia. In some cases, the method is performed to treat a hematopoietic system deficiency such as anemia, a myelodysplasia syndrome, a complication of chemotherapy, a complication of bone marrow donation, a complication of radiation therapy, leukemia, or lymphoma.

In some embodiments, the host receiving the transplant is a human subject. In some cases, the subject has received a chemotherapeutic treatment, or is a candidate for a chemotherapeutic treatment. In other cases, the subject has received a bone marrow transplant, umbilical cord blood transplant, or organ transplant, or is a candidate for a bone marrow transplant, umbilical cord blood transplant, or organ transplant. In some cases, the subject has depleted bone marrow, is a bone marrow donor, is deficient in HSCs, is anemic, or is otherwise in need of regeneration of the hematopoietic system.

In some embodiments, the cell therapy is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and expansion as provided herein are administered to the same subject.

In some embodiments, the cell therapy is carried out by allogeneic transfer, in which the cells are isolated and/or otherwise prepared from a subject other than a subject who is to receive or who ultimately receives the cell therapy, e.g., a first subject. In such cases, the cells, following ex vivo expansion, then are administered to a different subject, e.g., a second subject, of the same species. As used herein, the term "allogeneic" refers to a material that is genetically dissimilar but of the same species, which may be immunologically incompatible. In some embodiments, the first and second subjects are genetically identical. In some embodiments, the first and second subjects are genetically similar. In some embodiments, the second subject expresses the same HLA class as the first subject.

In some cases, the ex vivo expanded HSCs described herein are provided in a composition for cell therapy. Preferably, the composition is a pharmaceutical composition comprising expanded HSCs and a pharmaceutically acceptable carrier. A therapeutically effective amount of the pharmaceutical composition comprising the ex vivo expanded HSCs cells may be administered. As used herein, the term "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative. In some aspects, the choice of carrier is determined in part by the particular cell and/or by the method of administration. Accordingly, there are a variety of suitable formulations, and methods for preparing administrable pharmaceutical compositions are known.

Administration of ex vivo expanded HSCs may be carried out in any convenient manner known to those of skill in the art. In some cases, the cells are administered to a subject by aerosol inhalation, injection, ingestion, transfusion, implantation, or transplantation. The compositions described herein may be administered to a patient by intravenous (IV) injection, transarterially, subcutaneously, intradermally, intratumorally, intranodally, intramedullary, intramuscularly, or intraperitoneally. In other cases, the cells are injected directly into a particular site in the subject, a local disease site in the subject, an organ, and the like.

It will be advantageous in some cases to use one or more cell types derived from a particular mammalian subject (e.g., a particular human subject). In such cases, the cells may exhibit one or more specific phenotypes associated with or resulting from a particular disease or disorder of the particular mammalian subject. Subject-specific cells can be obtained or isolated from a tissue of interest (e.g., umbilical cord blood or bone marrow) by appropriate tissue sampling methods. In some cases, subject-specific cells are manipulated in vitro prior to contacting to a synthetic fetal liver organoid as described herein. For example, subject-specific cells can be expanded, differentiated, genetically modified, contacted to polypeptides, nucleic acids, or other factors, cryopreserved, or otherwise modified prior to use according to a method of this disclosure. In some cases, it will be advantageous to use cells derived from iPS cells obtained from individuals having known susceptibilities or resistances to various drugs or diseases for liver organoids of the disclosure. In such cases, liver organoids comprising subject-specific cells can be used to identify genetic factors and epigenetic influences that contribute to variable responses and that enhance hematopoietic expansion capacity.

Although human cells are preferred for use the methods and compositions of this disclosure, the cells are not to be limited to cells from human sources. Cells from other mammalian species including, but not limited to, equine, canine, porcine, bovine, feline, caprine, murine, and ovine sources can be used. Cell donors may vary in development and age. Cells can be derived from donor tissues of embryos, neonates, or older individuals including adults.

Engineered tissues and cell populations for use in clinical applications must be obtained in accordance with regulations imposed by governmental agencies such as the U.S. Food and Drug Administration. Accordingly, in exemplary embodiments, the methods provided herein are conducted in accordance with Good Manufacturing Practices (GMPs), Good Tissue Practices (GTPs), and Good Laboratory Practices (GLPs). Reagents comprising animal derived components are not used, and all reagents are purchased from sources that are GMP-compliant. In the context of preparing ex vivo expanded HSC populations for use in human cell therapies, GTPs govern cell donor consent, traceability, and infectious disease screening, whereas GMPs are relevant to the facility, processes, testing, and practices to produce consistently safe and effective products for human use. See Lu et al. *Stem Cells* 27: 2126-2135 (2009). Where appropriate, oversight of patient protocols by agencies and institutional panels is envisioned to ensure that informed consent is obtained; safety, bioactivity, appropriate dosage, and efficacy of products are studied in phases; results are statistically significant; and ethical guidelines are followed.

Articles of Manufacture

In another aspect, materials described herein, with or without additional materials, can be packaged together in any suitable combination as a kit useful for performing, or aiding in the performance of, a method provided herein. It is useful if the kit components in a given kit are designed and adapted for use together in the disclosed method. In some cases, the kit comprises ex vivo expanded HSCs produced according to the disclosed methods.

In another aspect, provided herein is a kit comprising one or more components useful for obtaining a substantially pure population of ex vivo expanded HSCs. Components of the kit can include one or more synthetic fetal liver organoids as described herein, one or more components for isolated HSCs from a donor, a chemically defined culture medium, and/or one or more medium additives such as a hematopoietic cytokine or growth factor. In some cases, the kit further comprises one or more components useful to prepare a synthetic fetal liver organoid for use according to the methods provided herein or components for genetically modifying cells of the fetal liver organoid or the expanded HSCs (e.g., one or more lentiviral constructs and/or CRISPR cassettes).

In interpreting this disclosure, all terms should be interpreted in the broadest possible manner consistent with the context. Unless defined otherwise, all technical and scientific terms used herein have the same meaning as commonly understood by one of ordinary skill in the art to which the invention belongs. It is understood that certain adaptations of the invention described in this disclosure are a matter of routine optimization for those skilled in the art, and can be implemented without departing from the spirit of the invention, or the scope of the appended claims.

As used in this specification and the appended claims, the singular forms "a," "an," and "the" include plural references unless the context clearly dictates otherwise. Any reference to "or" herein is intended to encompass "and/or" unless otherwise stated.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

The terms "comprising", "comprises" and "comprised of" as used herein are synonymous with "including", "includes" or "containing", "contains", and are inclusive or open-ended and do not exclude additional, non-recited members, elements, or method steps. The phraseology and terminology used herein is for the purpose of description and should not be regarded as limiting. The use of "including," "comprising," "having," "containing," "involving," and variations thereof, is meant to encompass the items listed thereafter and additional items. Embodiments referenced as "comprising" certain elements are also contemplated as "consisting essentially of" and "consisting of" those elements. Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements.

The terms "about" and "approximately" shall generally mean an acceptable degree of error for the quantity measured given the nature or precision of the measurements. Typical, exemplary degrees of error are within 10%, and preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The invention will be more fully understood upon consideration of the following non-limiting Examples. All papers and patents disclosed herein are hereby incorporated by reference as if set forth in their entirety.

EXAMPLES

The following sections demonstrate the inventors' unique methods for maintaining and expanding patient-derived HSCs ex vivo.

Example 1—Ex Vivo Expansion of HSCs on Synthetic Fetal Liver Organoids

Figures 17A, 17B, 17C, 17D:
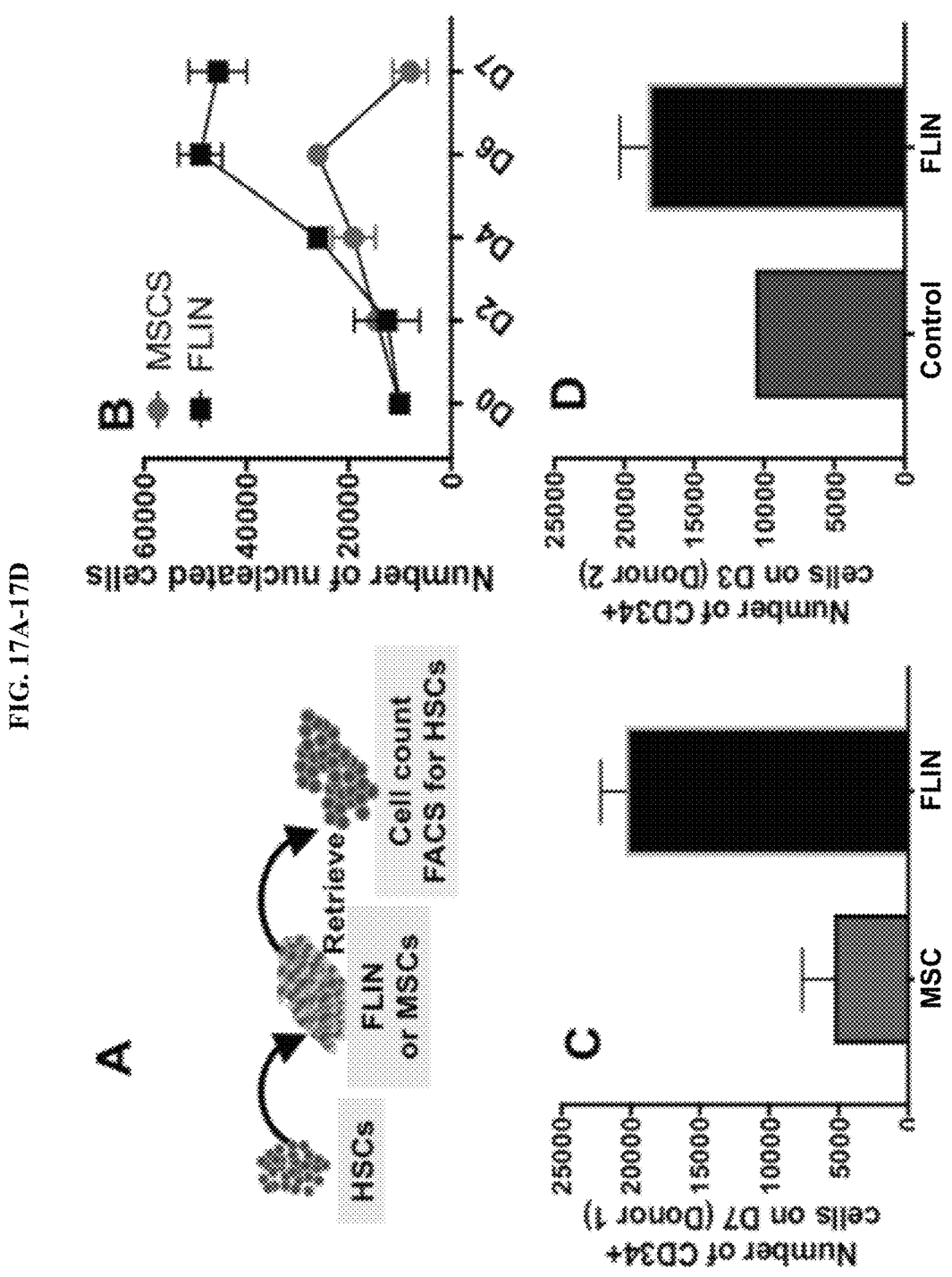
FIGS. 17A-17D demonstrate HSC expansion in FLINs. (A) Schematic of an experiment. (B) FLIN outcompetes MSCs to support HSC expansion over 7 days. (C) Higher number of CD34$^+$ cells expanded on FLIN tissue compared with MSC feeder control (donor 1, D7) or (D) no-feeder HSC only controls (donor 2, D3) as assessed via FACS analysis.

Multiple cell types contribute to HSC expansion and differentiation in vivo, but the identities and function of each cell type remain unclear. To determine whether FLINs can act as a niche to support hematopoiesis ex vivo, umbilical cord-derived HSCs were contacted to and cultured on GATA6-engineered vascularized human FLINs. Specifically, a day-10 FLIN was seeded with approximately $10^4$ CD34$^+$ HSCs derived from umbilical cord blood. The seeded organoid was cultured for about 7 to about 10 days or more. For these assays, the seeded organoids were cultured in the presence of a fully defined, serum-free and animal component-free ("xeno-free") basal culture medium such as STEMdiff™ APEL™ medium (StemCell Technologies). Based on our previous data (Guye et al., *Nature Comm.* 2016, 7:10243), this medium supports the development and maintenance of FLINs up to at least a month. During the culture period, the culture medium was partially changed (50%) daily. CD34$^+$ cells were retrieved and a total nucleated cell count and flow cytometry for CD34$^+$ cells were performed. As shown in FIGS. 17A-17B, FLINs promoted the self-renewal and expansion of CD34$^+$ cells better than both MSC control cells as well as the no-feeder control.

Figure 24:
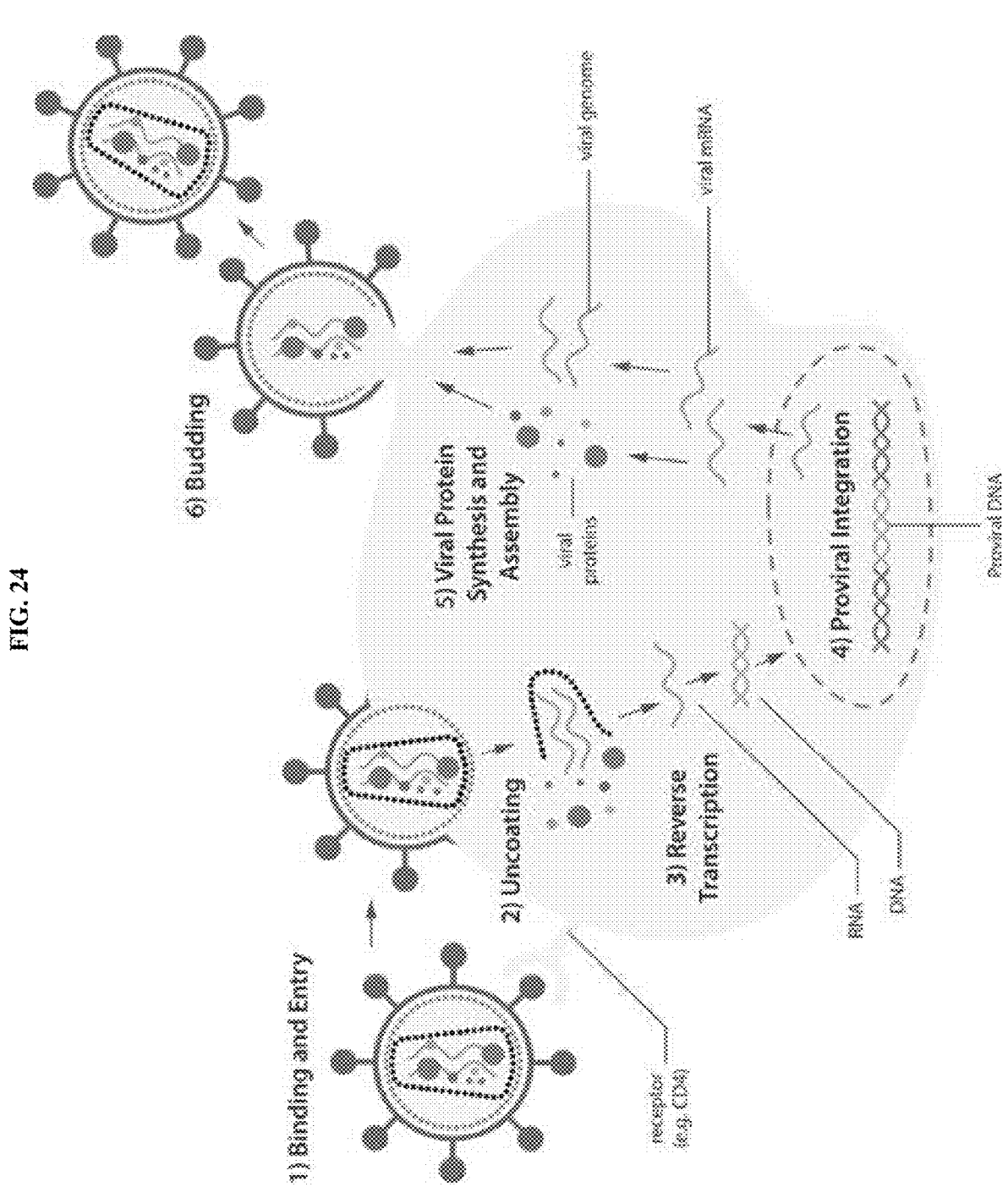
FIG. 24 is a schematic illustration of genetic engineering via a lentiviral vector system, which is random, irreversible, and limited to approximately 10 kb payload (provirus size).
Figure 25:
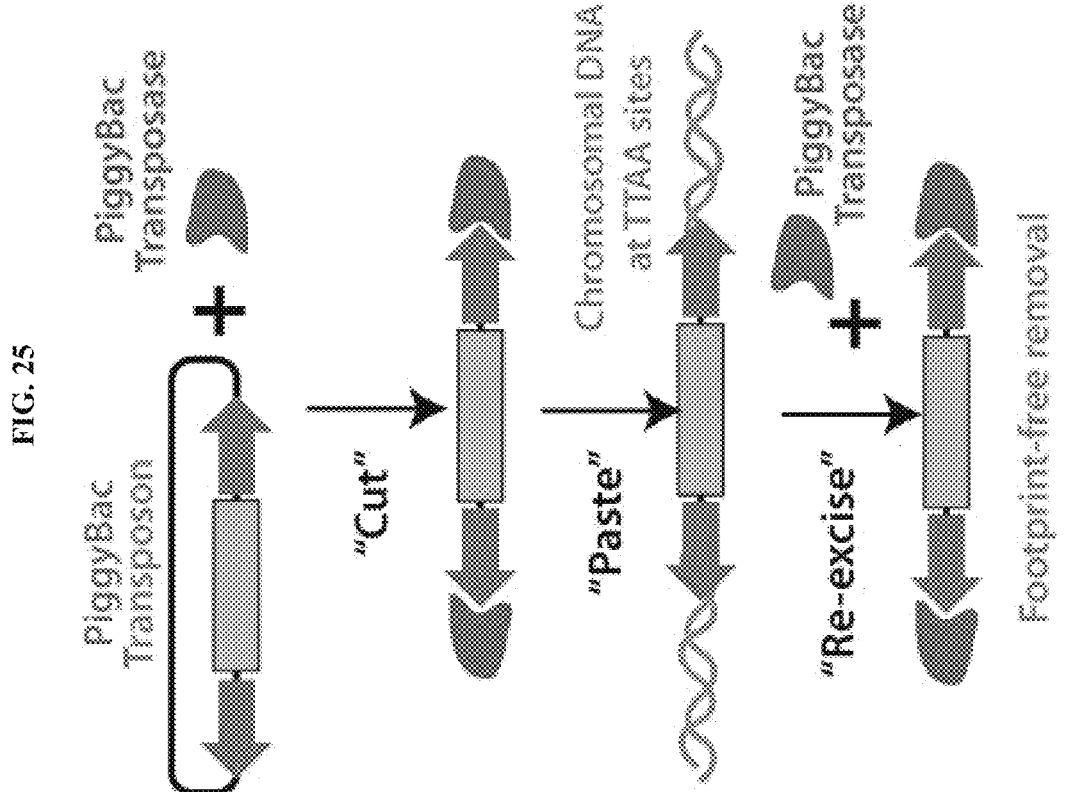
FIG. 25 is a schematic illustration of genetic engineering via a Piggybac genetic engineering system, which is predictable, reversible, and has a large carrying capacity (>200 kb).

To maximize payload capacity and use a predictable and reversible gene editing tool, a Piggybac transposon system was for generation of cell lines described herein. FIGS. 24 and 25 illustrate how the Piggybac engineering system mitigates challenges associated with genetic engineering using lentiviral vectors. rtTA expressing PGP1 hiPSCs previously generated (Guye et al., 2016) were transfected using Lipofectamine 3000 (ThermoFisher Scientific) with Super PiggyBac Transposase (System Biosciences) and the PiggyBac transposon vector with hGATA6-2A-EGFP under control of the tetracycline responsive element promoter. Transfected cells were selected by adding 0.5 μg/mL puromycin to the mTeSR1 maintenance medium. See Velazquez and LeGraw et al., 2020 (BioRxiv 2020, DOI: 10.1101/2020.05.10.087445) for additional information on generation and characterization of FLIN (referred to as FeLO in the aforementioned manuscript).

Figure 3:
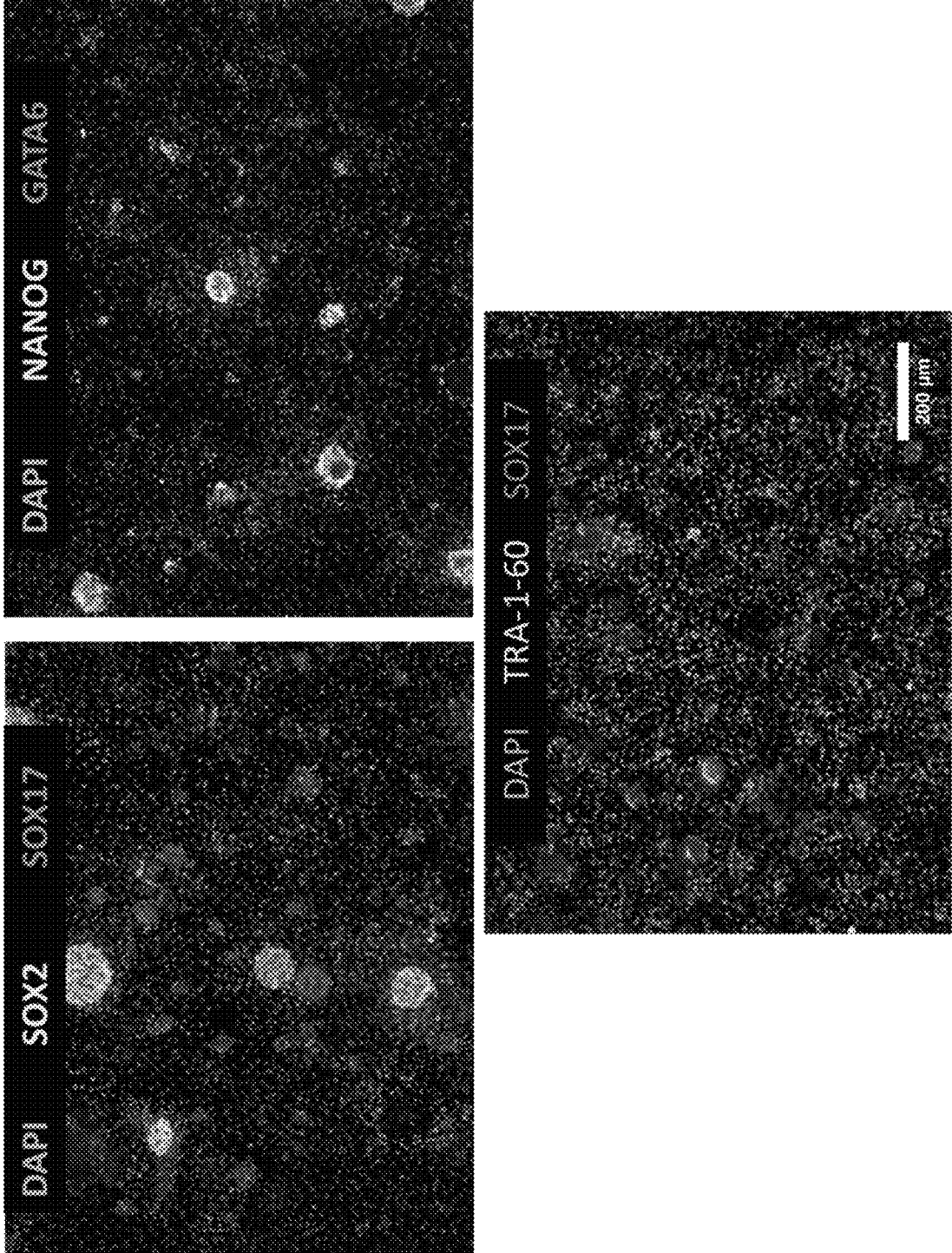
FIG. 3 demonstrates that, five days post induction, GATA6 and SOX17 are expressed in nearly all cells indicating the exit of the pluripotent state and differentiation towards mesendoderm. A small portion of pluripotent cells as determined by expression of NANOG, SOX2, and TRA-1-60 remain.
Figure 4:
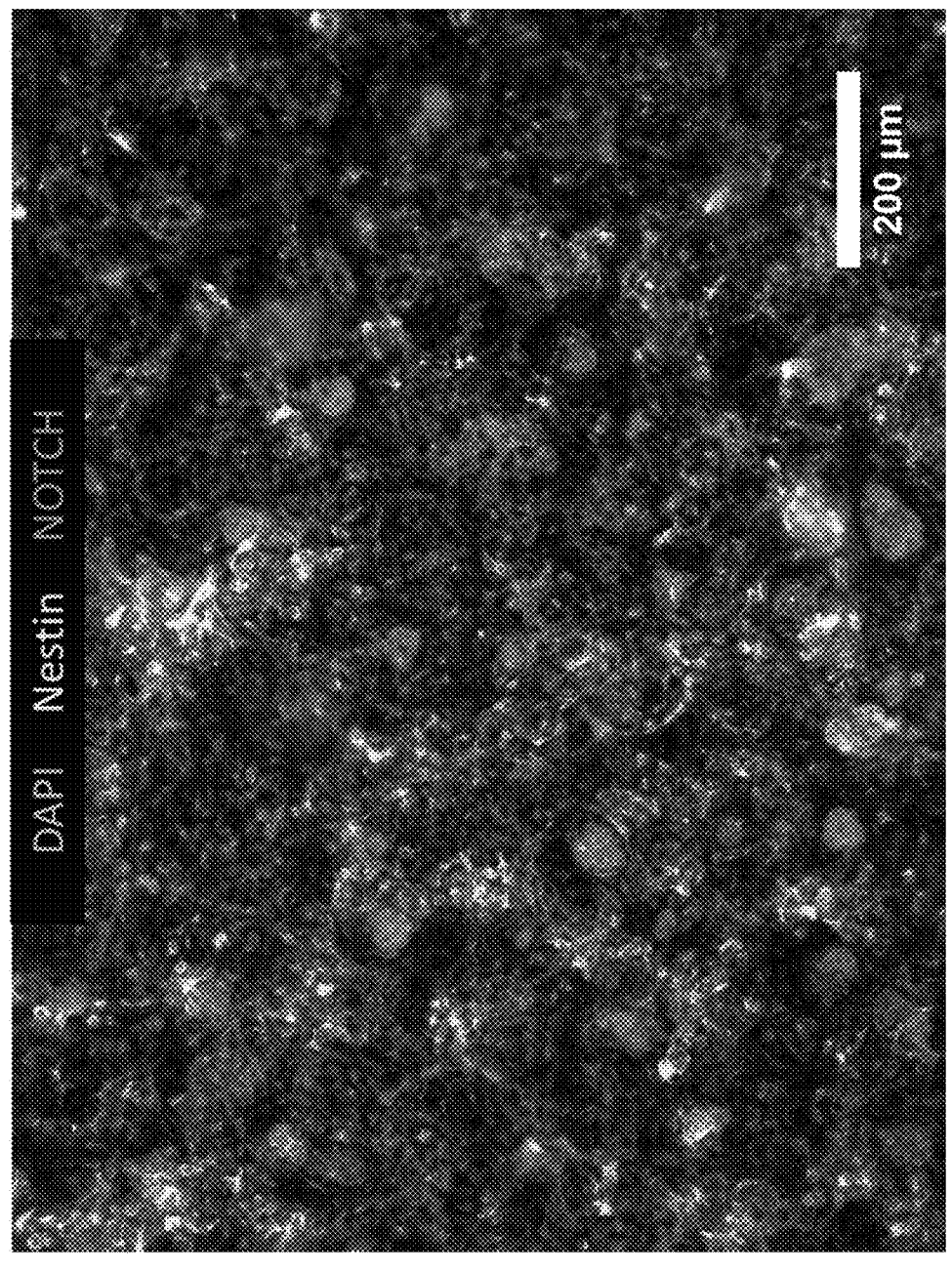
FIG. 4 demonstrates that, by Day 5 post-induction, FLINs can supply hematopoietic niche signaling such as NOTCH signaling and they contain Nestin positive cells.
Figure 7A:
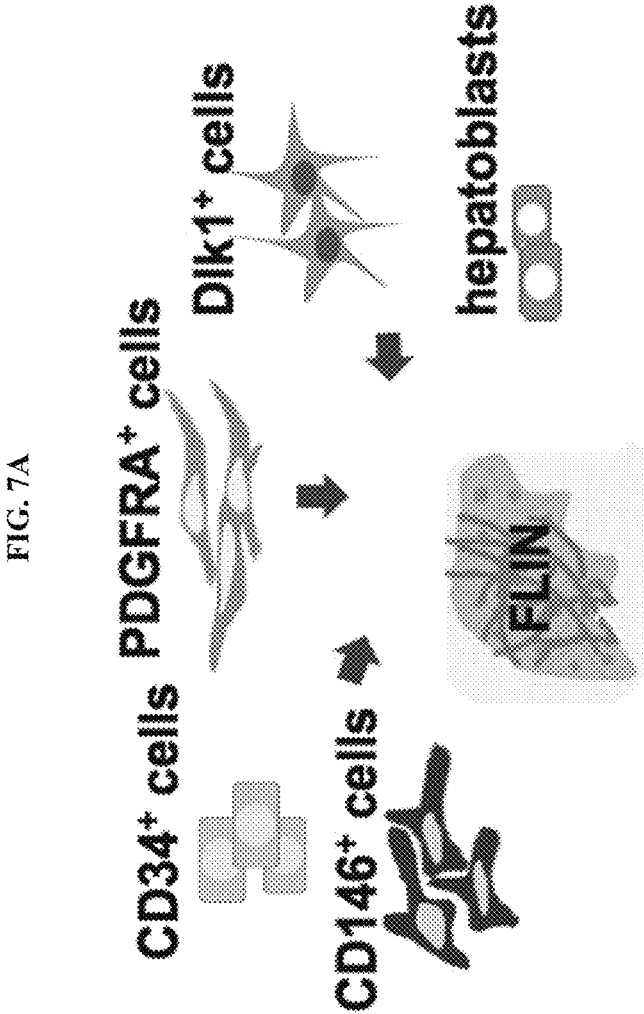
FIG. 7A illustrates cell populations in FLIN cellular compositions which are reported to function as niche cells for HSCs.
Figures 7B, 7C:
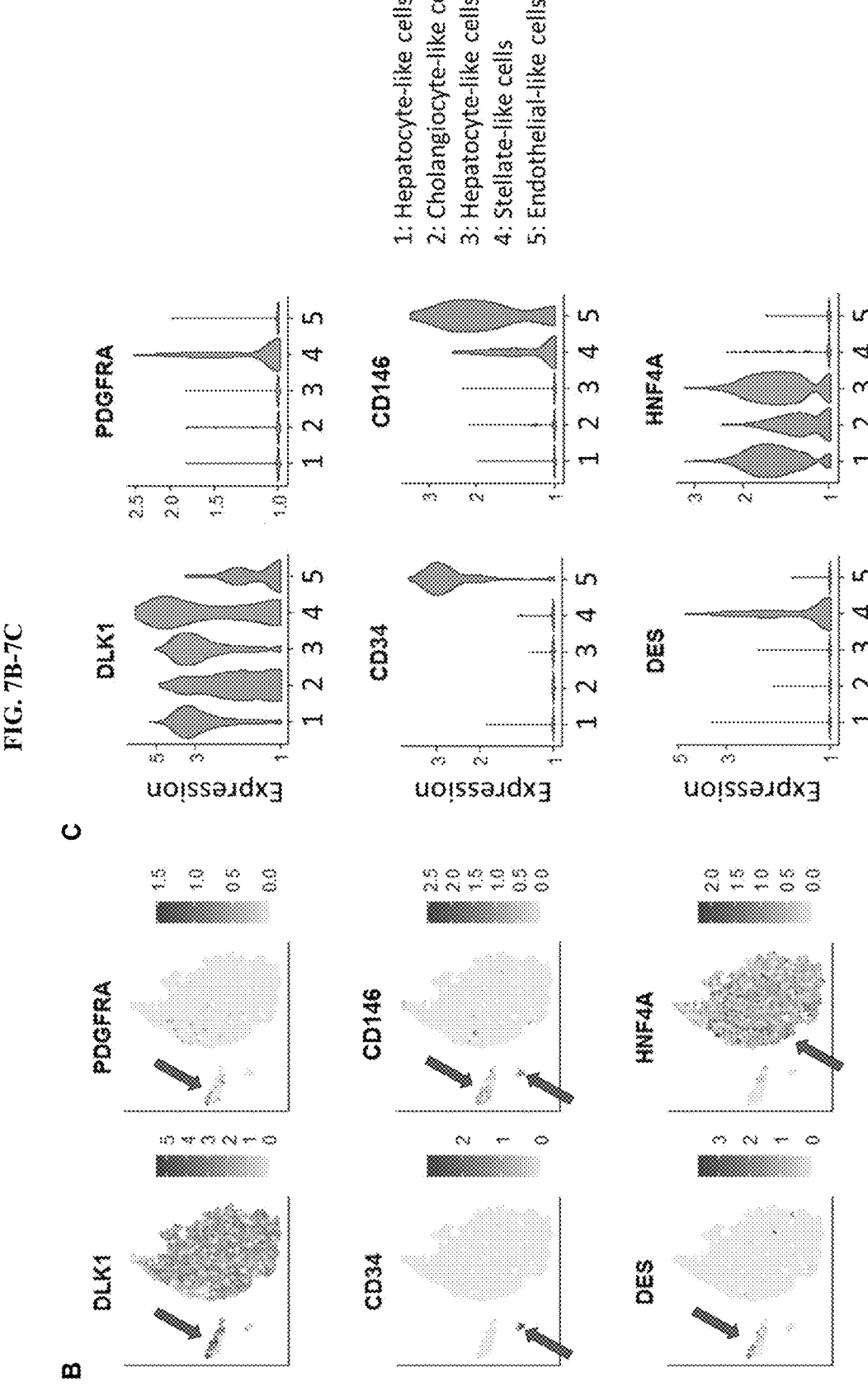
FIG. 7B presents T-distributed Stochastic Neighbor Embedding (t-SNE) plots of FLIN niche genes expressed in populations indicated by the red arrows.
FIG. 7C presents violin plots showing the expression of FLIN niche genes within hepatocyte-like, cholangiocyte-like, stellate cell-like, and endothelial cell-like characterized sub-populations.

As shown in FIG. 3, GATA6 and SOX17 are expressed in nearly all cells at five days post induction, indicating the exit of the pluripotent state and differentiation towards mesendoderm. A small portion of pluripotent cells remained, as determined by expression of NANOG, SOX2, and TRA-1-60. FIG. 4 demonstrates that by Day 5 post-induction, FLINs supplied hematopoietic niche signaling such as NOTCH signaling and they contain Nestin positive cells. Furthermore, FIG. 5 demonstrates that Desmin-expressing pericyte-like cells localized with the CD31-expressing endothelium.

Figure 9:
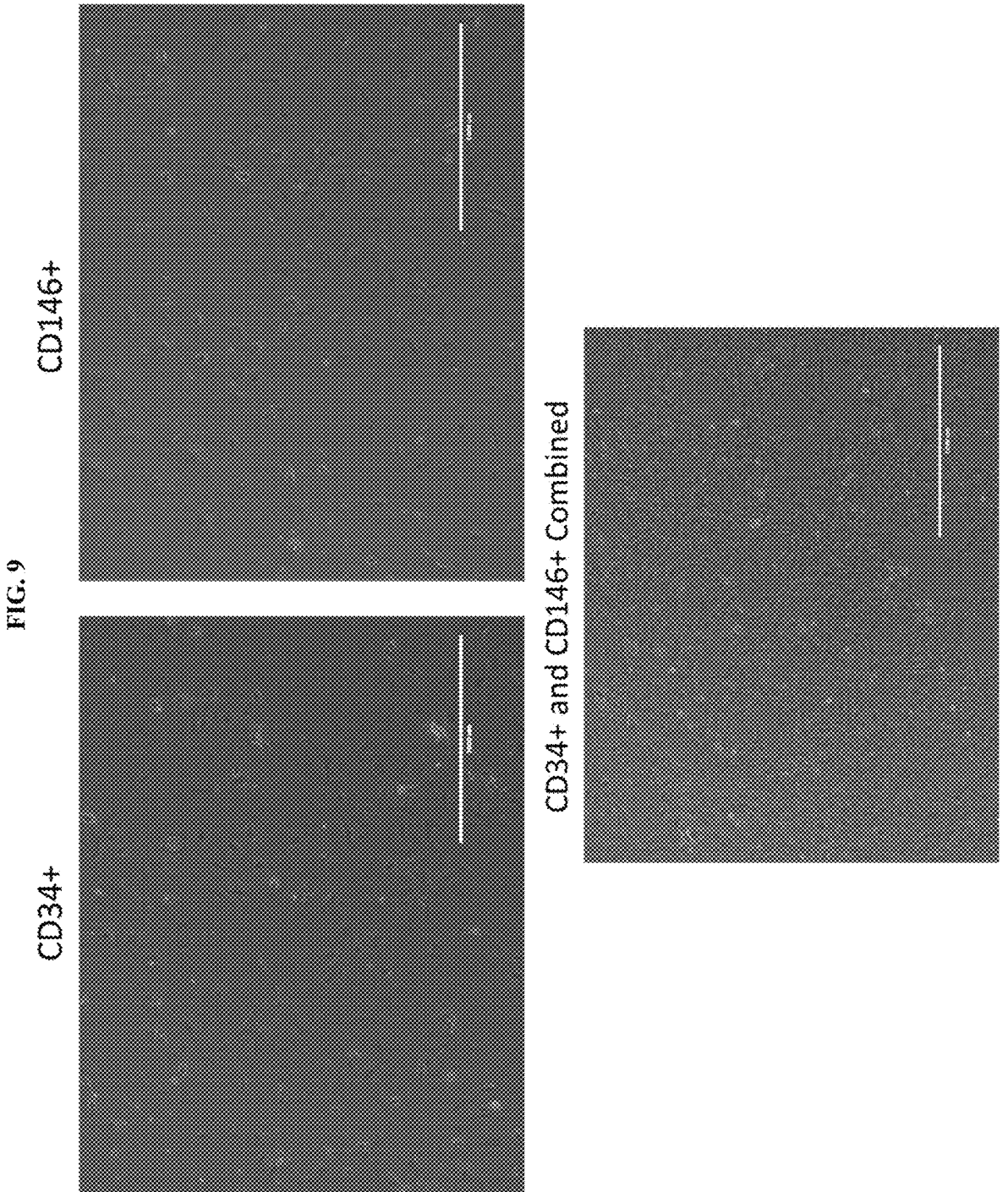
FIG. 9 presents images of CD34+, CD146+, and combined CD34+ and CD146+ cell populations isolated from FLIN using magnetic beads. These populations represent cell populations found in the fetal liver that have been implicated in HSC expansion. This provide ability to generate, isolate and maintain these cell populations in vitro for HSC expansions.

As shown in FIG. 9, CD34+, CD146+, and combined CD34+ and CD146+ cell populations were isolated from FLIN using magnetic beads. These populations represent cell populations found in the fetal liver that have been implicated in HSC expansion in vivo. This suggests that the presence of these cell populations could play a role in HSC expansion in FLIN.

Figure 10:
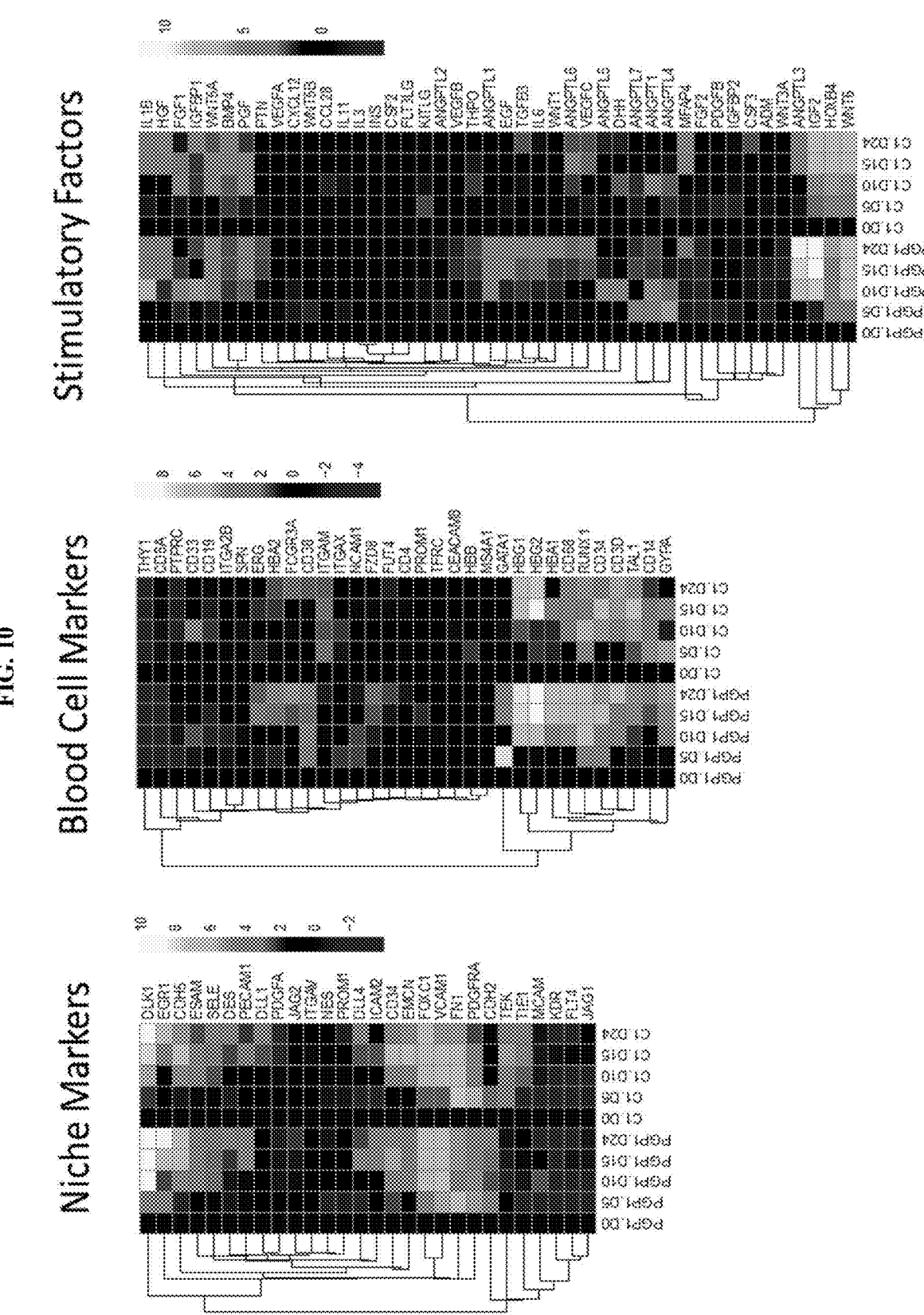
FIG. 10 presents heatmaps showing gene expression levels of select fetal liver niche identity markers, blood cell identity markers, and stimulatory factors for HSC expansion in the following conditions: undifferentiated (D0) iPSC, day 5 (D5) PGP1-line and C1-line FLIN, day 10 (D10) PGP1 and C1 FLIN, day 17 (D17) PGP1 and C1 FLIN, and day 24 (D24) PGP1 and C1 FLIN. PGP1 and C1 are two different hiPSC lines.

FIG. 10 presents heatmaps showing gene expression levels of select fetal liver niche identity markers, blood cell identity markers, and stimulatory factors for HSC expansion in the following conditions: undifferentiated (D0) iPSC, day 5 (D5) PGP1 and C1 FLIN, day 10 (D10) PGP1 and C1 FLIN, day 17 (D17) PGP1 and C1 FLIN, and day 24 (D24) PGP1 and C1 FLIN.

Figure 11A:
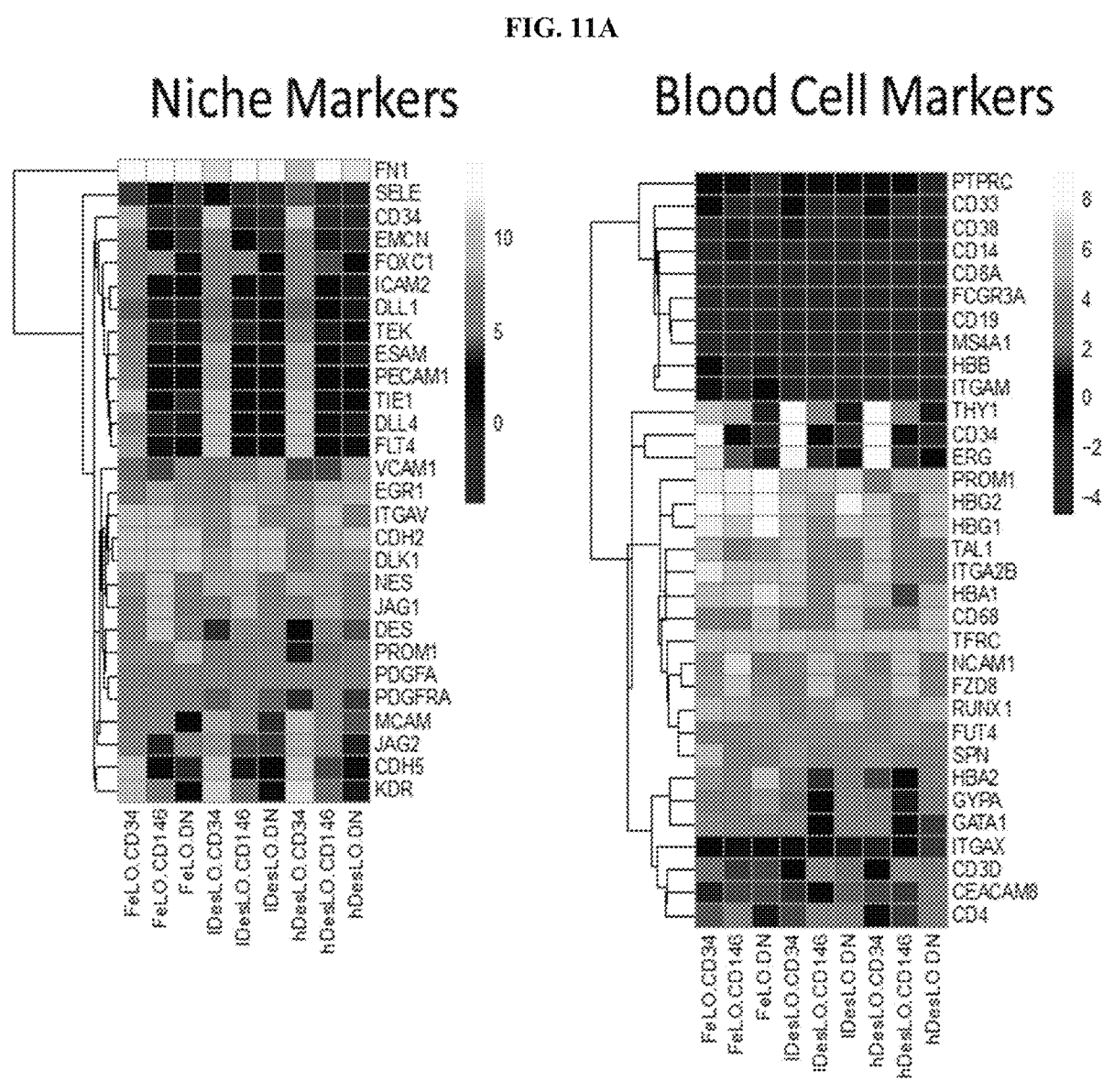

FIG. 11A is a set of heatmaps showing gene expression levels of select fetal liver niche identity markers and blood cell identity markers for HSC expansion. Conditions include CD34+, CD34−CD146+, and CD34−/CD146− double negative cells isolated using magnetic beads (Miltenyi Biotech) from FLIN, low MOI DesLO (iDesLO), and high MOI DesLO (hDesLO). These populations represent cell populations found in the fetal liver. "DesLO" contain ATF, PROX1 and CRISPR-based activation of CYP3A4 for inducing liver maturation.

Figure 11B:
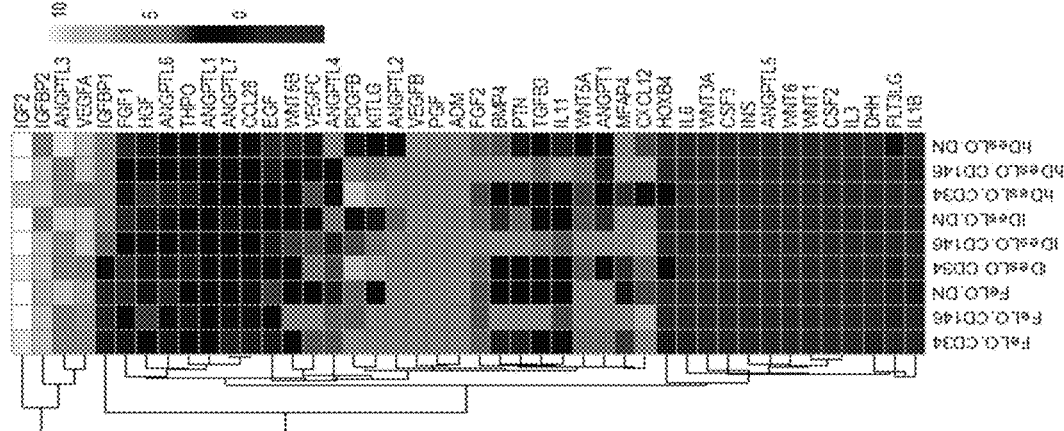
FIG. 11B is a set of heatmaps showing gene expression levels of select stimulatory and inhibitory factors for HSC expansion. Conditions include CD34+, CD34−CD146+, and CD34−/CD146− double negative cells isolated using magnetic beads (Miltenyi Biotech) from FLIN. Low MOI DesLO (lDesLO), and high MOI DesLO (hDesLO) shows FLIN that is additionally engineered via over expression of ATF5, PROX1 and CRISPR based activation of CYP3A4 to ignite maturation of fetal liver. These populations represent cell populations found in the fetal liver. The data shows presence of wide variety of signals important for HSC homeostasis.

FIG. 11B is a set of heatmaps showing gene expression levels of select stimulatory and inhibitory factors for HSC expansion. Conditions include CD34+, CD34−CD146+, and CD34−/CD146− double negative cells isolated using magnetic beads (Miltenyi Biotech) from FLIN, low MOI DesLO (lDesLO), and high MOI DesLO (hDesLO). These populations represent cell populations found in the fetal liver.

FIG. 12 presents qPCR data demonstrating upregulation of the hematopoietic cytokines FLT3LG and THPO following transduction of the FLIN with lentiviral expression vectors for FLT3LG only, THPO only, or FLT3LG and THPO together.

Figure 13:
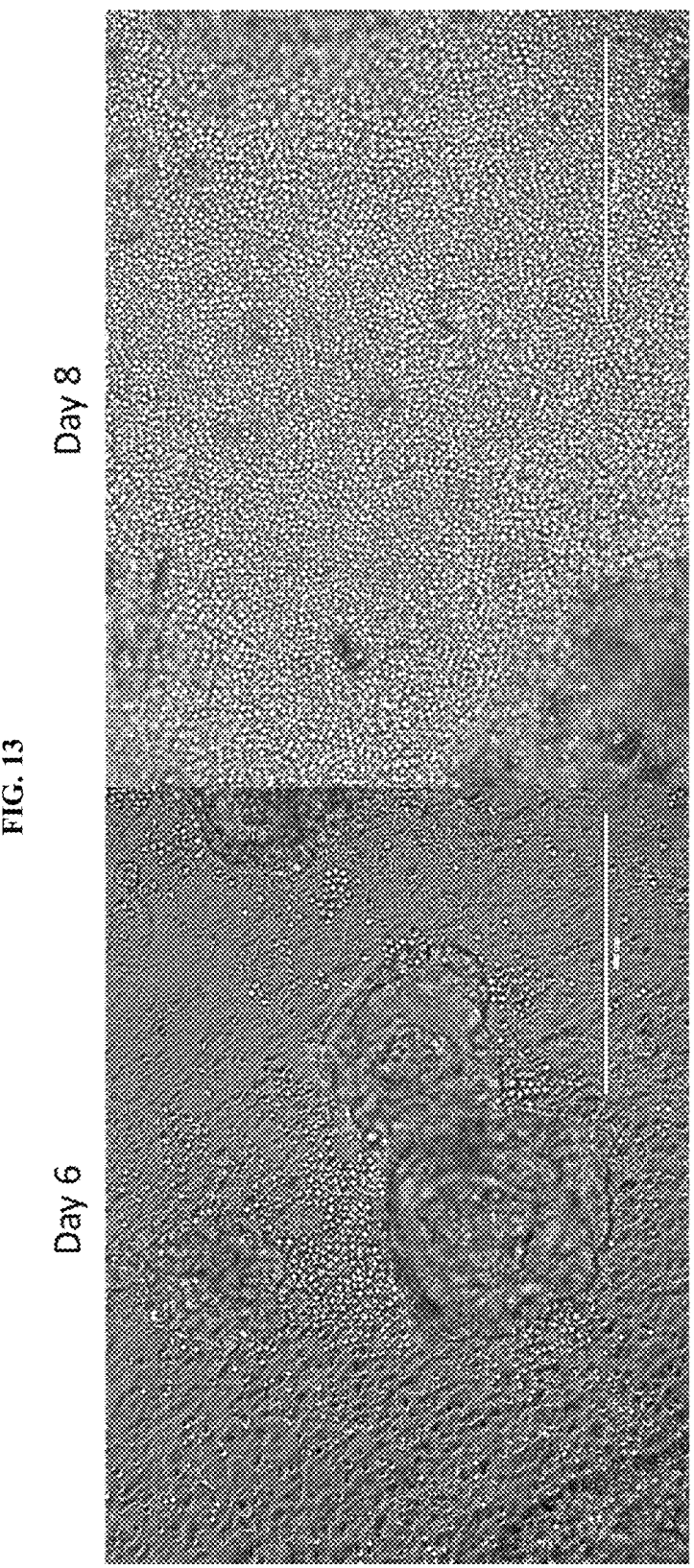
FIG. 13 presents phase microscopy images showing expansion of small, round, white, cord blood-derived hematopoietic cells between days 6 and 8 of co-culture with FLIN. This demonstrates proliferation of the cord blood-derived hematopoietic cells can happen rapidly when co-cultured with FLINs.

As shown in FIG. 13, co-cultured HSCs expanded from day 6 to day 8 of co-culture, as determined by phase microscopy. The images show expansion of small, round, white, cord blood-derived hematopoietic cells between days 6 and 8 of co-culture with FLIN. These data demonstrate proliferation of the cord blood-derived hematopoietic cells can happen rapidly when co-cultured with FLINs.

Figure 14:
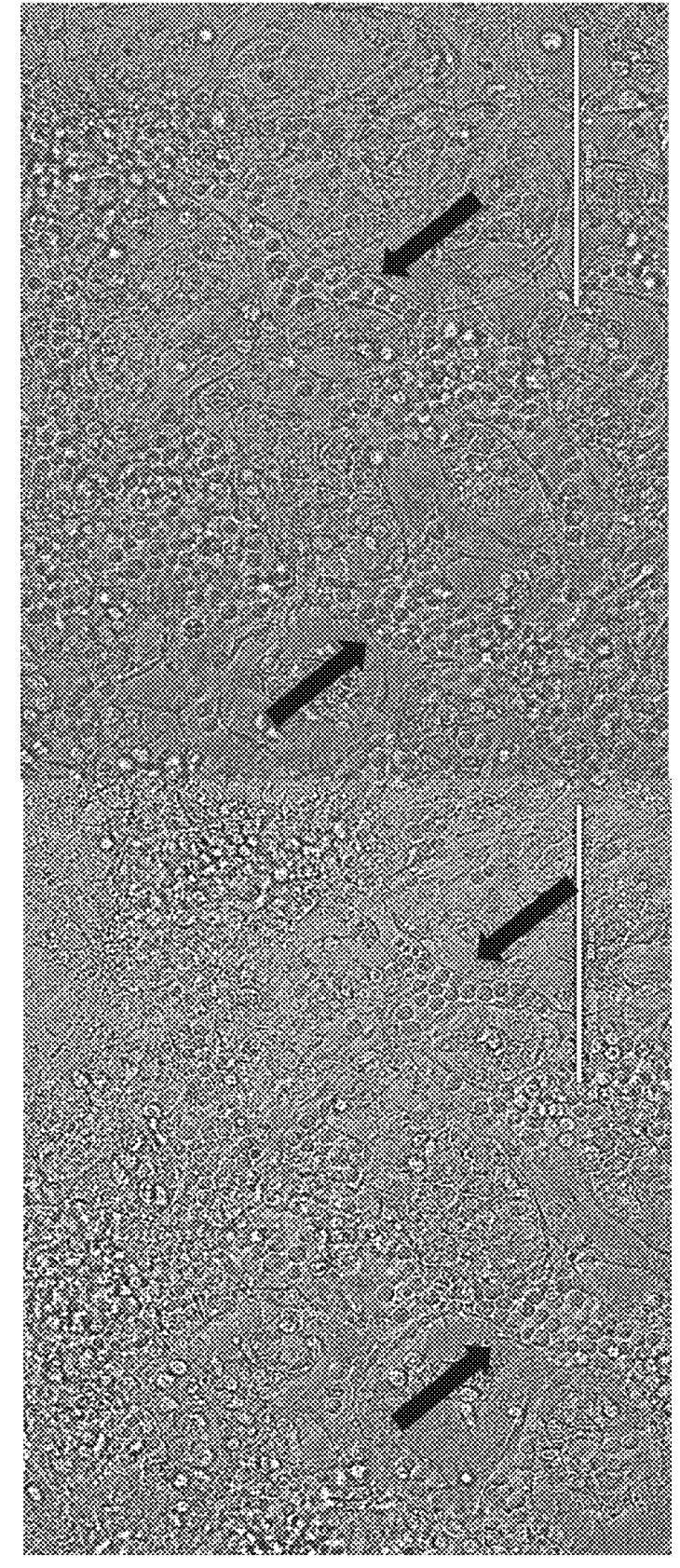
FIG. 14 presents images showing small round hematopoietic cells integrating into vasculature of FLIN, thus demonstrating the unique cellular interactions that occur between the co-cultured cells that may contribute to the HSC expansion phenotype.
Figure 16:
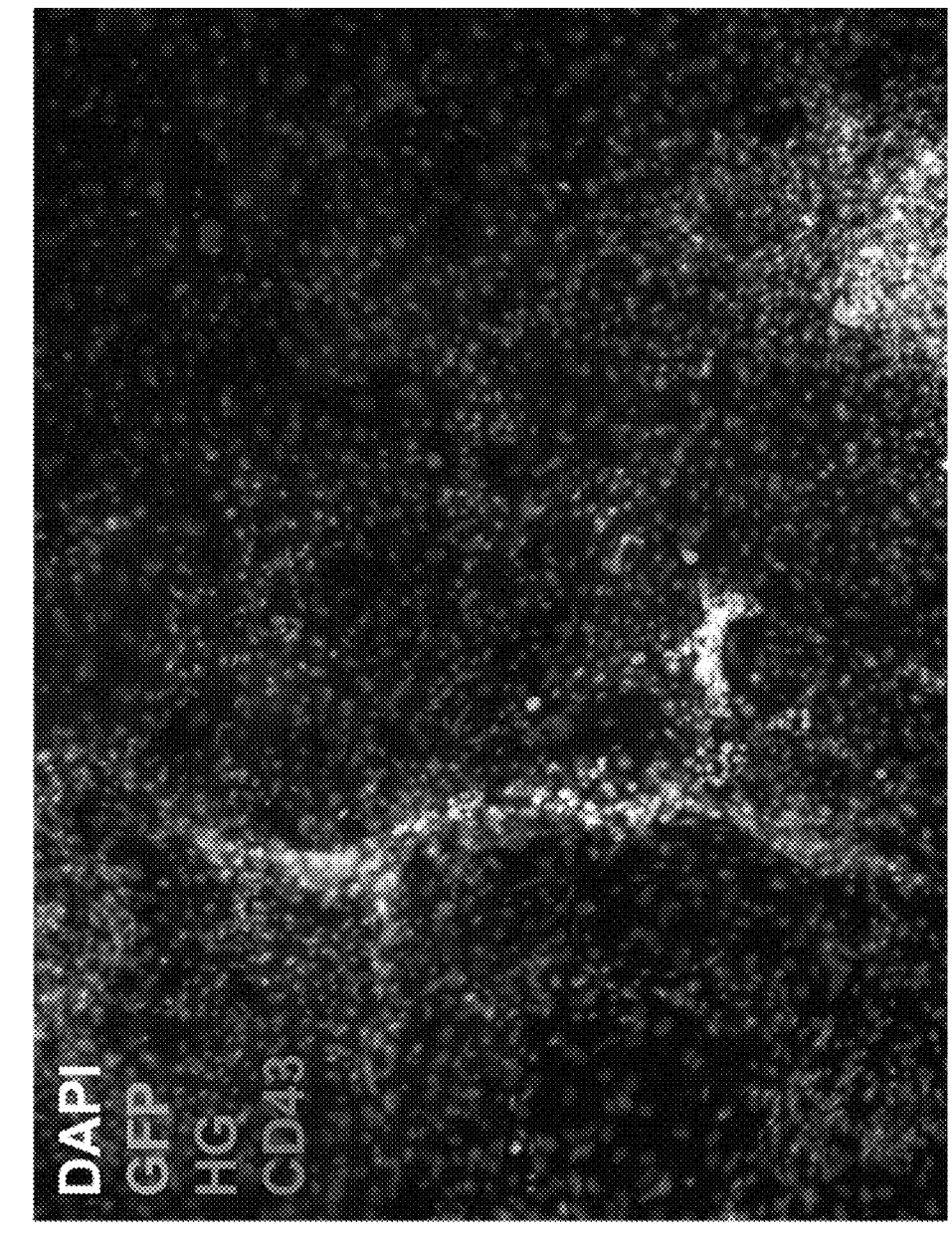
FIG. 16 demonstrates the presence of pockets of hemoglobin (HG) positive cells in FLIN co-cultures after 7 days. These HG+ structures are similar to blood islands found in the embryonic yolk sac from which erythrocyte progenitors and later HSCs emerge, suggesting that the FLIN tissue is conducive to harboring HSCs.

As shown in FIG. 14, small round hematopoietic cells integrate into vasculature of FLINs, thus demonstrating the unique cellular interactions that occur between the co-cultured cells that may contribute to the HSC expansion phenotype. Human CD34+ cord blood-derived HSCs co-cultured for 7 days on FLIN showed expansion of hematopoietic progenitor cells marked by CD43 expression among the prominent CD34+ vascular beds (FIG. 15). As shown in FIG. 16, pockets of hemoglobin (HG) positive cells were detected in FLIN co-cultures after 7 days. These HG+ structures are similar to blood islands found in the embryonic yolk sac from which erythrocyte progenitors and later HSCs emerge, suggesting that the FLIN tissue is conducive to harboring HSCs.

Figure 19:
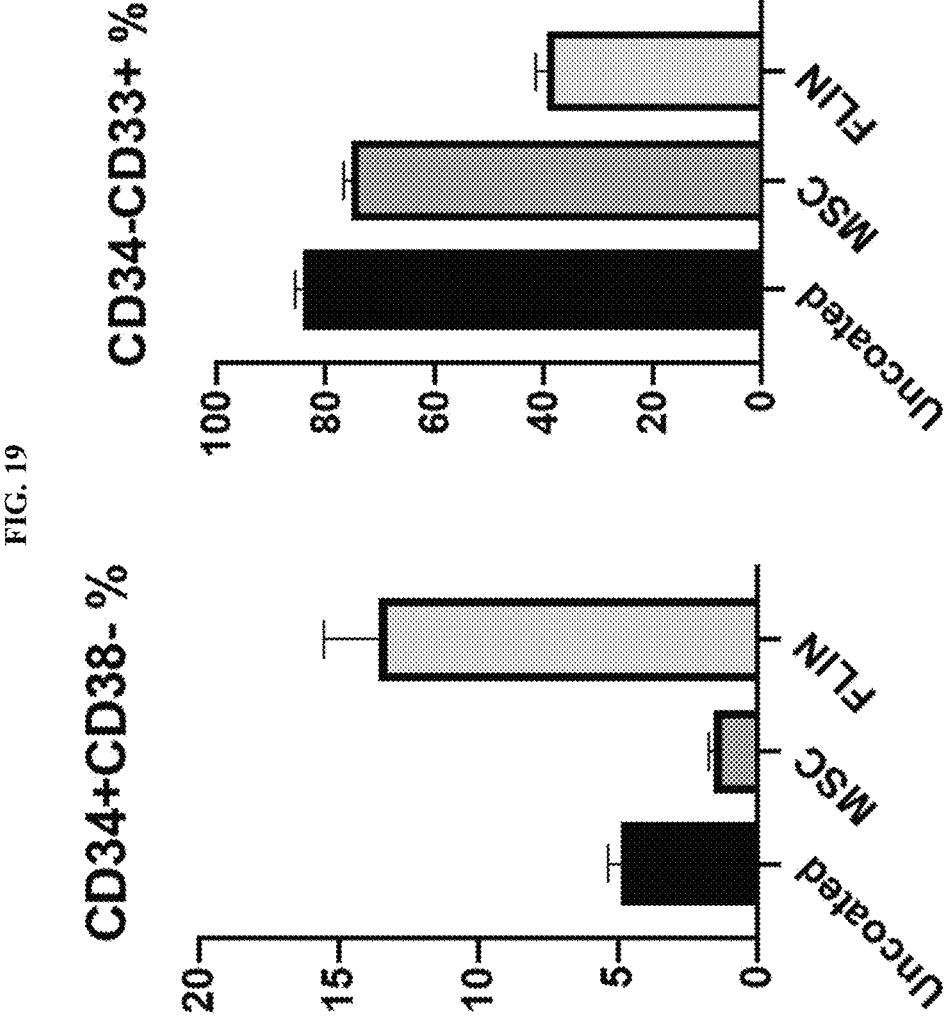
FIG. 19 shows cell populations of interest from day 10 flow cytometry data, shown as a percent of total live leukocyte-like cells (gating shown in in FIGS. 21A-C and FIGS. 22A-22C). CD34+CD38− is enriched for HSCs compared to total population. CD34−CD33+ represent myeloid progenitors. These data demonstrate that the HSC enriched subset is more prevalent in FLIN co-cultures, and that the cells in FLIN co-cultures have a lower myeloid bias, which demonstrates higher potential for generation of alternative lineages.

Daily total cell counts for CD34+ cells seeded into uncoated plates, into MSC co-cultures, and into FLIN co-cultures demonstrated that the greatest increase in total cell numbers occurred in FLIN co-cultures (FIG. 18). FIG. 19 shows cell populations of interest from day 10 flow cytometry data, shown as a percent of total live leukocyte-like cells. CD34+CD38− cells were enriched for HSCs compared to total population. CD34−CD33+ represent myeloid progenitors. These data demonstrate that the HSC enriched subset is more prevalent in FLIN co-cultures, and that the cells in FLIN co-cultures have a lower myeloid bias, which demonstrates higher potential for generation of alternative lineages.

Figure 20:
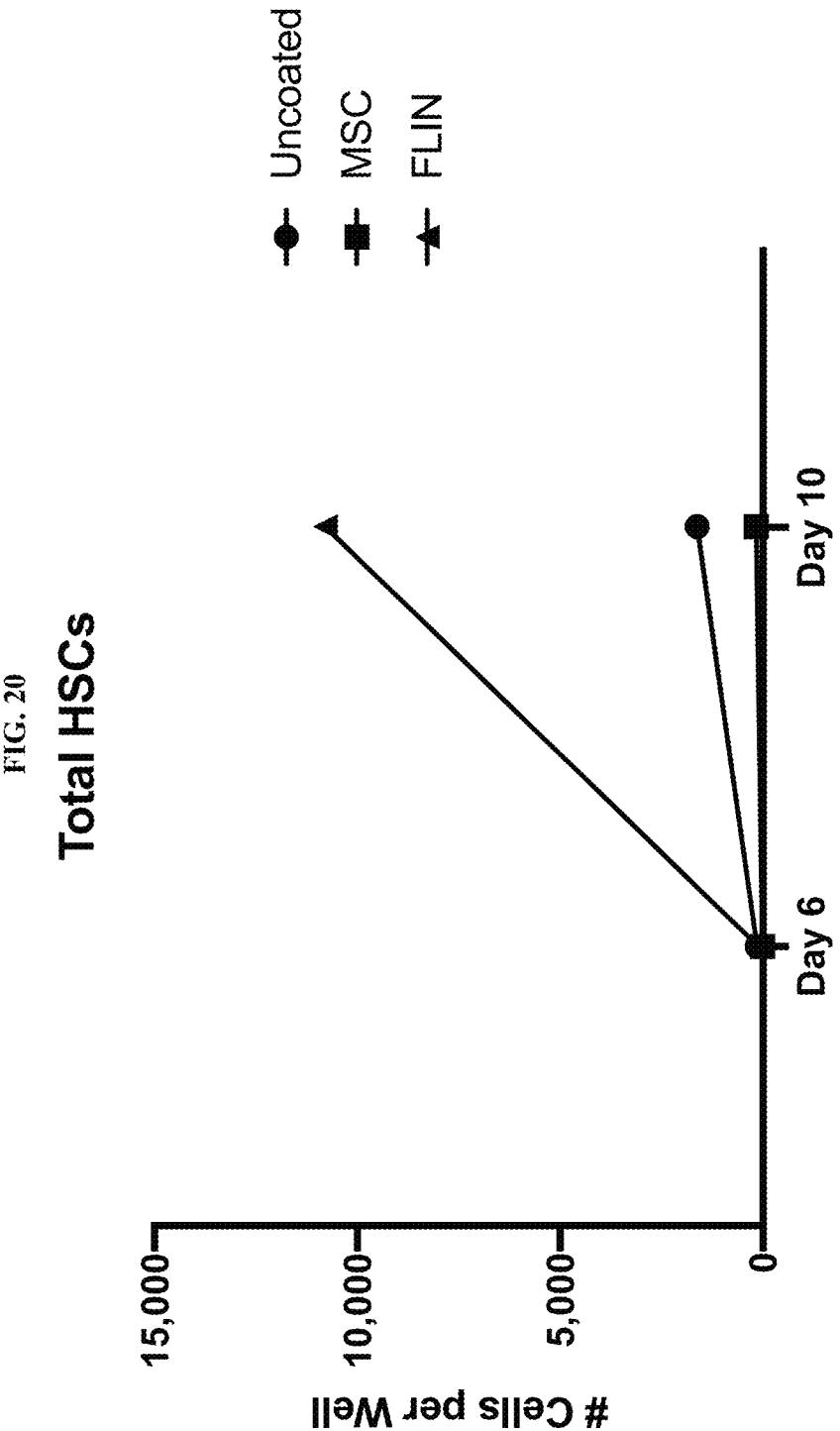
FIG. 20 demonstrating that total HSC expansion was highest in FLIN co-cultures. The graph represents the total number of HSCs present per well in uncoated plates, MSC co-cultures, and FLIN co-cultures.
Figure 21A:
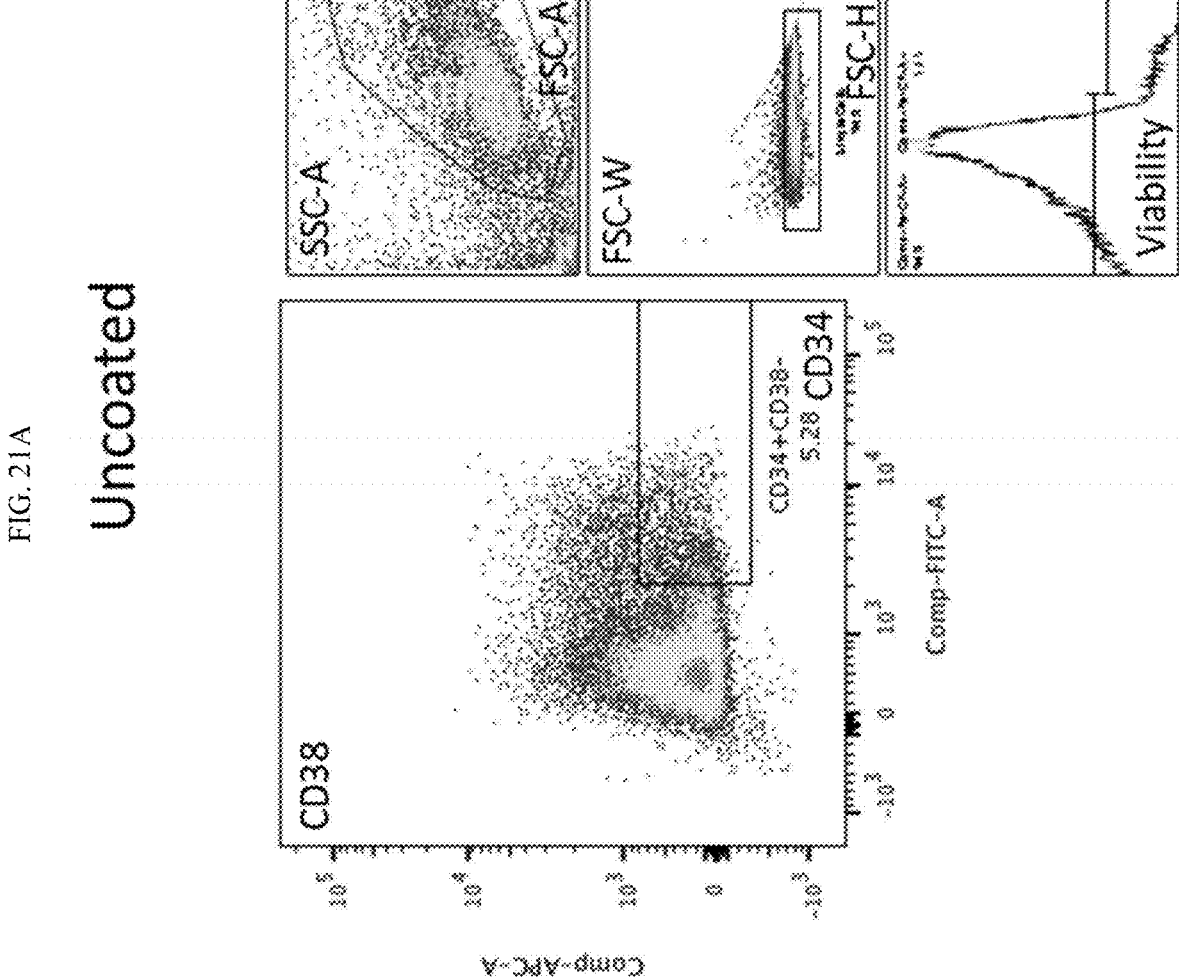
FIG. 21A demonstrates flow cytometry gating strategy for CD34+CD38− cells on uncoated plates. Leukocyte-like cells are selected from FSC-A vs SSC-A. Single cells are selected from FSC-H vs FSC-W. Viable cells are selected from negative staining of the 7-AAD viability dye. CD34+CD38– cells are selected from CD34 vs CD38.
Figure 21B:
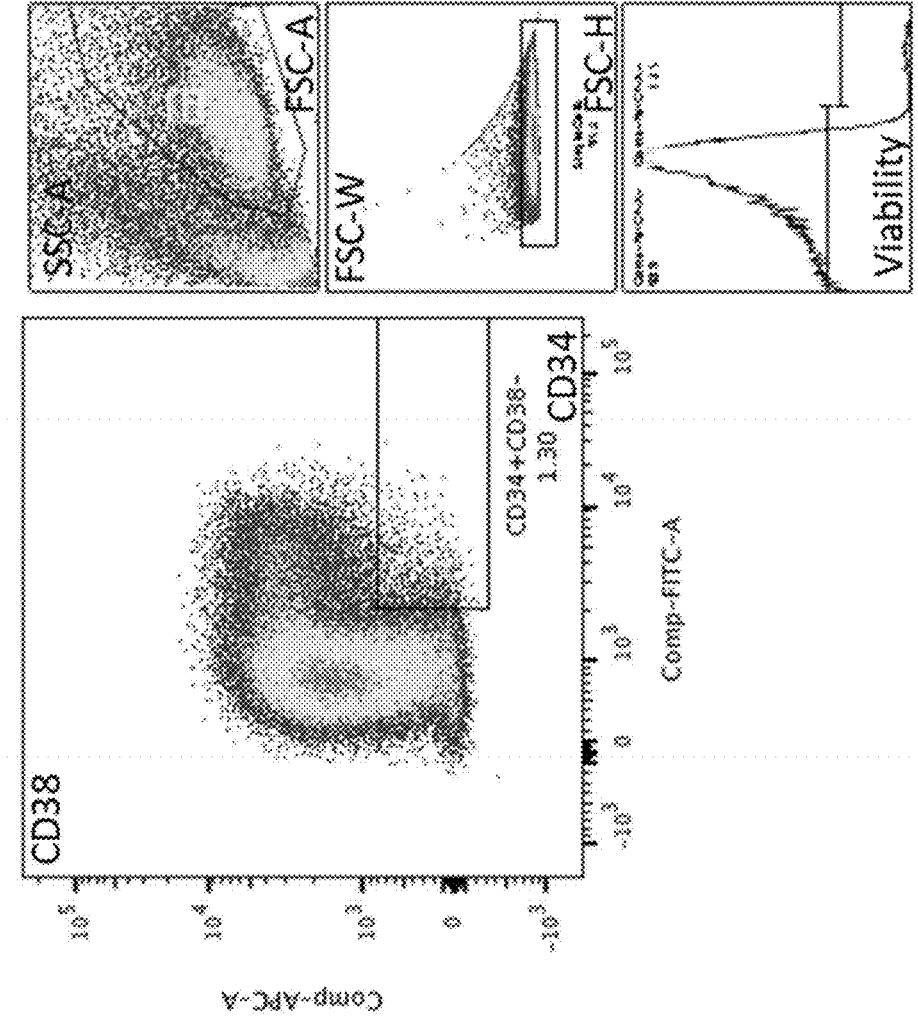
FIG. 21B demonstrates flow cytometry gating strategy for CD34+CD38– cells on MSC co-cultures. Leukocyte-like cells are selected from FSC-A vs SSC-A. Single cells are selected from FSC-H vs FSC-W. Viable cells are selected from negative staining of the 7-AAD viability dye. CD34+ CD38– cells are selected from CD34 vs CD38.
Figure 21C:
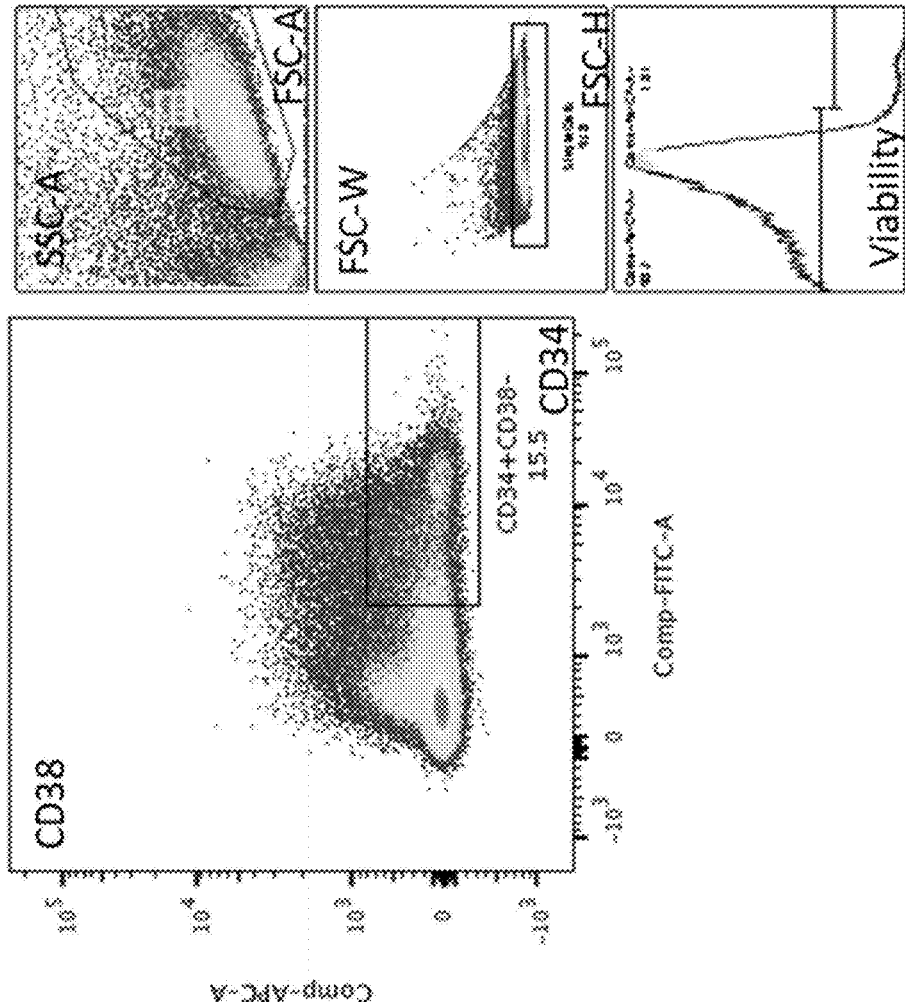
FIG. 21C demonstrates flow cytometry gating strategy for CD34+CD38– cells on FLIN co-cultures. Leukocyte-like cells are selected from FSC-A vs SSC-A. Single cells are selected from FSC-H vs FSC-W. Viable cells are selected from negative staining of the 7-AAD viability dye. CD34+ CD38– cells are selected from CD34 vs CD38.
Figure 22A:
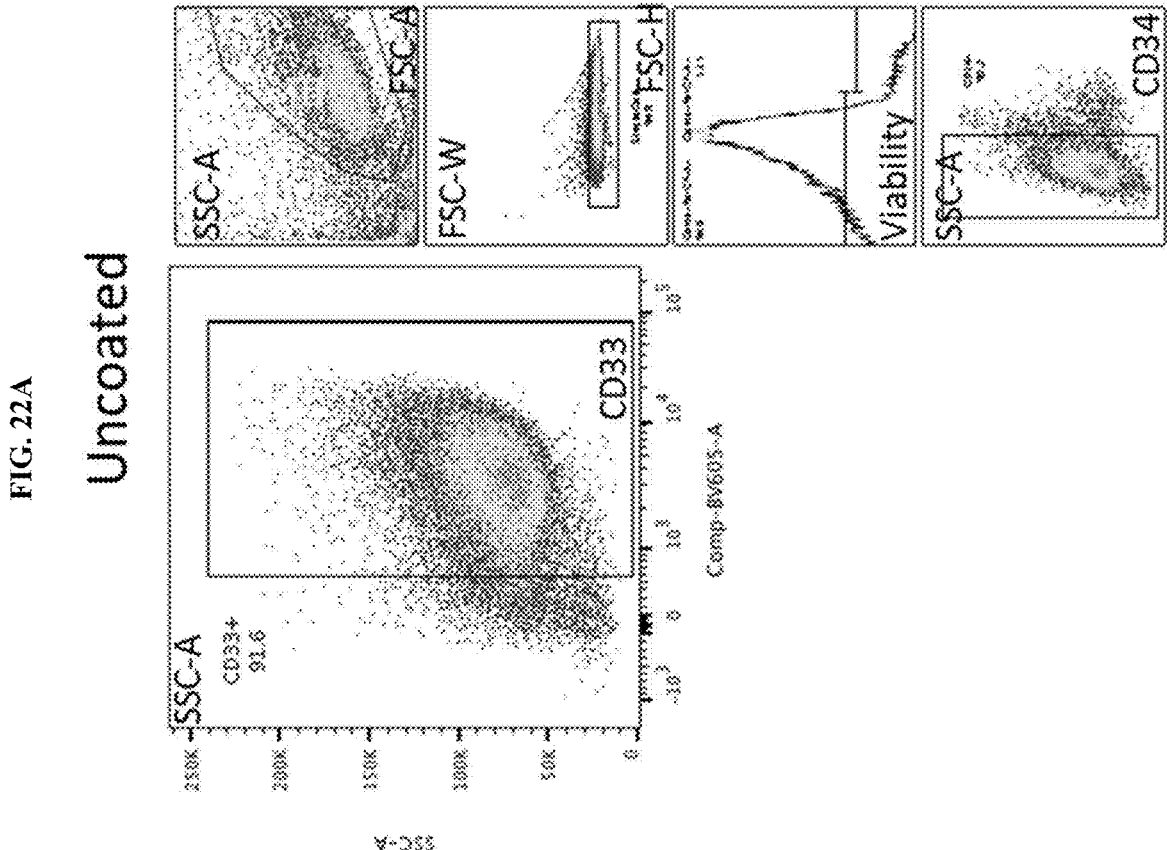
FIG. 22A demonstrates flow cytometry gating strategy for CD34-CD33+ cells on uncoated plates. Leukocyte-like cells are selected from FSC-A vs SSC-A. Single cells are selected from FSC-H vs FSC-W. Viable cells are selected from negative staining of the 7-AAD viability dye. CD34– cells are selected from CD34 vs SSC-A. CD33+ cells are selected from CD33 vs SSC-A.
Figure 22B:
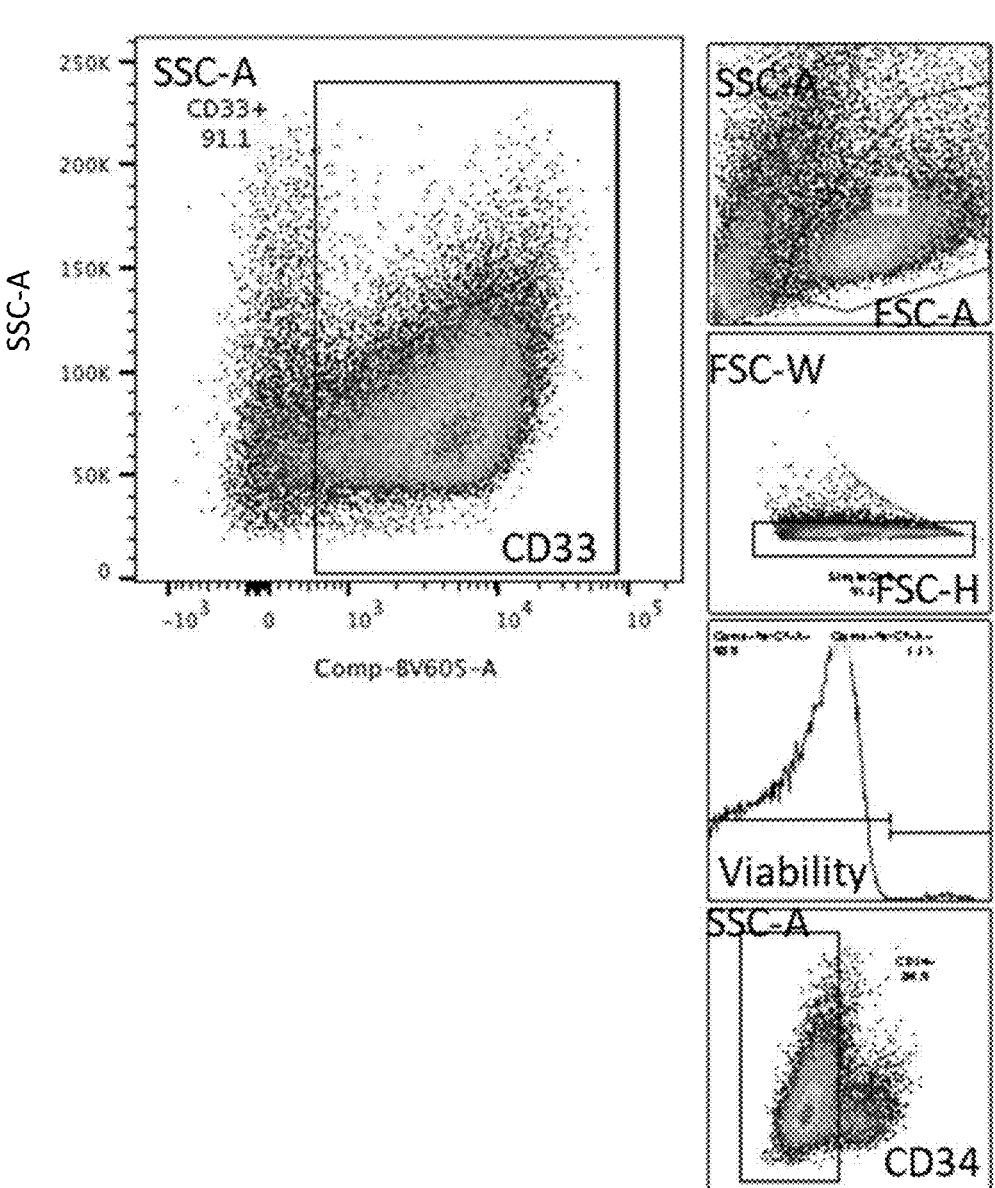
FIG. 22B demonstrates flow cytometry gating strategy for CD34–CD33+ cells on MSC co-cultures. Leukocyte-like cells are selected from FSC-A vs SSC-A. Single cells are selected from FSC-H vs FSC-W. Viable cells are selected from negative staining of the 7-AAD viability dye. CD34– cells are selected from CD34 vs SSC-A. CD33+ cells are selected from CD33 vs SSC-A.
Figure 22C:
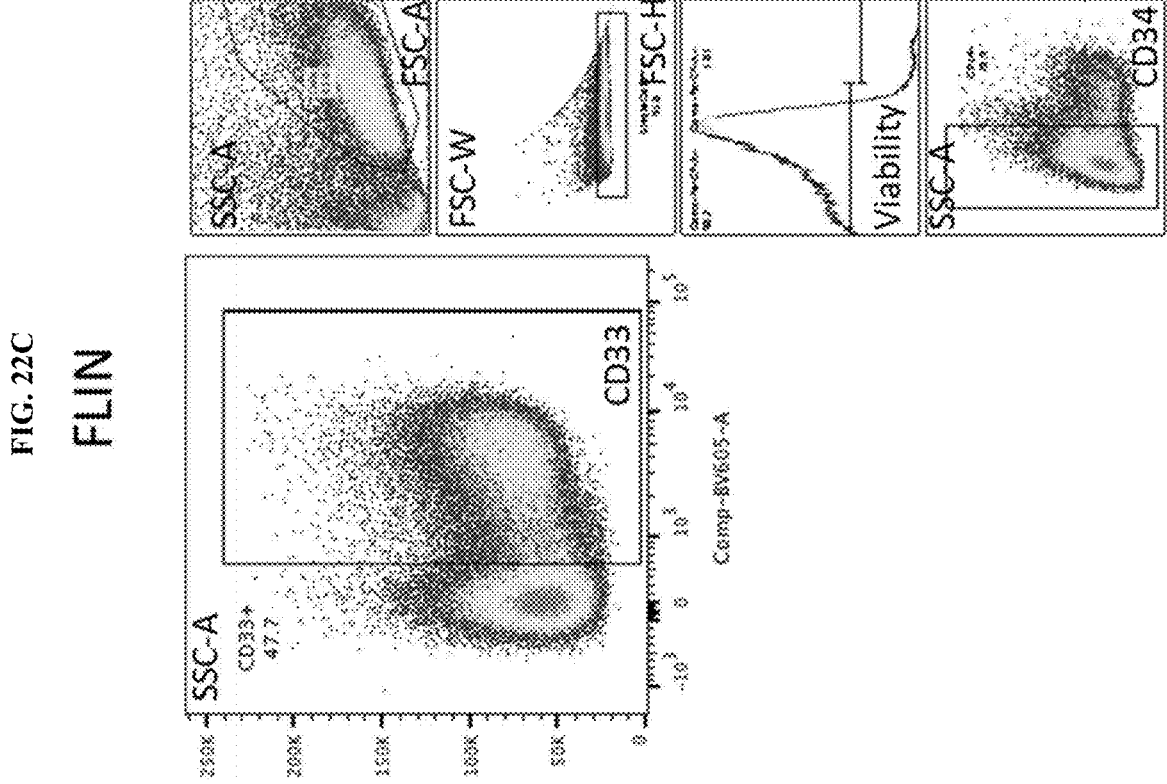
FIG. 22C demonstrates flow cytometry gating strategy for CD34–CD33+ cells on FLIN co-cultures. Leukocyte-like cells are selected from FSC-A vs SSC-A. Single cells are selected from FSC-H vs FSC-W. Viable cells are selected from negative staining of the 7-AAD viability dye. CD34– cells are selected from CD34 vs SSC-A. CD33+ cells are selected from CD33 vs SSC-A.

It was observed that total HSC expansion was highest in FLIN co-cultures (FIG. 20). Flow cytometry was performed, gating for CD34+CD38– cells on uncoated plates (FIG. 21A), on MSC co-cultures (FIG. 21B), and on FLIN co-cultures (FIG. 21C). Gating for CD34–CD33+ myeloid progenitors is shown in FIGS. 22A-22C.

Example 2—Scalability of FLIN HSC Cultures Using Microcarriers

Microcarrier cultures afford high surface-to-volume ratios thereby leading to efficient utilization of medium/factors and lower bioprocess costs. Cells on the surface of compact microcarriers assume a monolayer-like configuration with direct exposure to media, as with formation of FLIN as demonstrated before. A Gata6-based FLIN formation on microcarrier beads was obtained. The inducible, heterogeneous, and transient expression of a GATA6 transgene in the engineered hiPSC line for five days in mTesR medium induces the differentiation and self-organization of meso-dermal and endodermal lineages. After cessation of induced GATA6 expression, the culture medium was changed to IMDM supplemented with fetal bovine serum (FBS), which directs the tissue to differentiate towards a fetal liver niche phenotype. After five days of IMDM/FBS, the culture medium is further supplemented with the hematopoietic cytokines SCF, FLT3 ligand, and thrombopoietin. This step further induces differentiation of hematopoietic lineages in culture and creates an environment in which cord blood cells can interact with the FLIN cells to induce proliferation of the hematopoietic stem cells. Additionally, at the time in which the culture medium is changed to IMDM/FBS, the FLINs can also be enzymatically dissociated to single cells and reseeded following transduction with lentiviral expression vectors for expression of cytokines, transcription factors, or other genetic elements which remove the need for cytokine supplementation or to induce customizable changes in the FLIN microenvironment.

An exemplary microbead seeding protocol is as follows: On day 5 following dox induction, FLIN cultures were brought into a single cell suspension with accutase, washed in basal medium and suspended in 1 mL of mTeSR culture medium containing 1 μg/mL doxycycline and 30 μM Y-27632 (ROCK inhibitor) at a cell density of about 1 million cells per mL in a 5 mL round bottom polystyrene tube pre-prepared with about 2000 Matrigel-coated cytodex 3 beads. The tubes were flicked every 15 minutes for 4 hours to allow the cells to coat the beads. Cell-coated beads were then distributed evenly into round bottom 96-well plates promote aggregation, then cultured as regular FLIN. Cultures stained on day 14 of culture show support of the CD34+ endothelial cells and AAT+ hepatic cells in this format (FIG. 6).

Figures 8A, 8B:
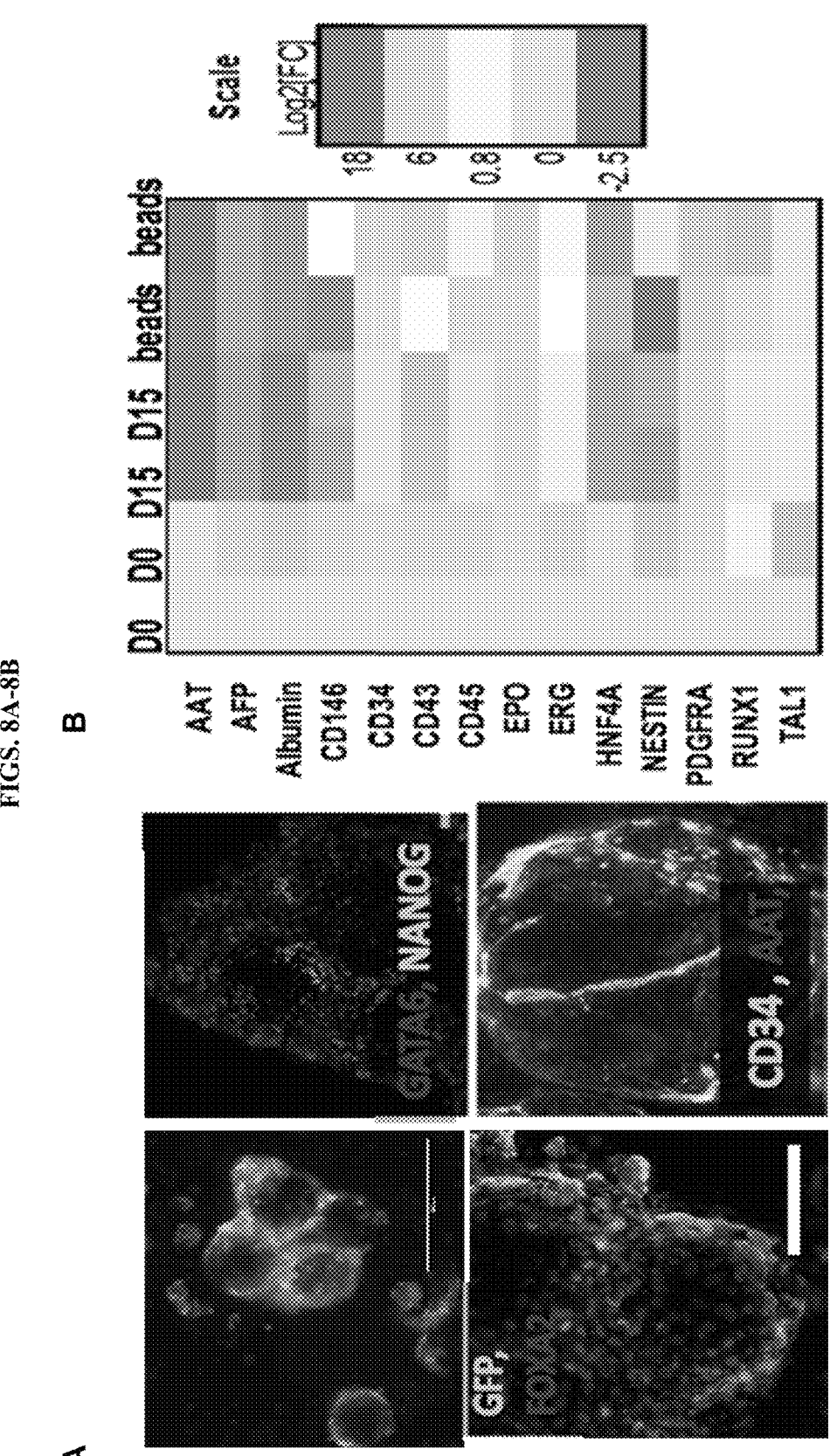
FIGS. 8A-8B demonstrate microcarrier culture of FLINs. (A) FLIN culture of Matrigel-coated beads forms endoderm by day 3 (panel A top and bottom left). Panel A bottom right shows generation of vascularized FLIN on D15. (B) Quantitative PCR analyses show slightly augmented hematopoietic signature in FLIN developed on beads (e.g., RUNX1).

The microcarrier-based FLINs exhibited a comparable fetal liver phenotype to conventional FLIN tissue (FIG. 8A). In particular, FLINs cultured on Matrigel-coated beads form endoderm by day 3 (FIG. 8A, top and bottom left). FIG. 8A bottom right shows generation of vascularized FLIN on day 15. Interestingly, quantitative PCR analysis revealed an increase of hematopoietic markers such as CD43, ERG, and RUNX1 in FLIN on the microcarrier beads (FIG. 8B). These data demonstrate the feasibility of co-culturing HSCs on microcarrier-based FLIN.

We claim:

1. A method for ex vivo expansion of human hematopoietic stem cells (HSCs), the method comprising (a) contacting a cell population comprising the human HSCs with a synthetic fetal liver organoid comprising mesenchymal-like cells, CD34-expressing (CD34+) endothelial-like cells, desmin-expressing (DES+) stellate-like cells, and CEBPα+ hepatocyte-like cells, wherein at least a portion of cells of the synthetic fetal liver organoid are genetically modified to express one or more of Stem Cell Factor (SCF), FMS-like Tyrosine Kinase 3 Ligand (FLT3L), and Thrombopoietin (TPO); and (b) culturing the contacted organoid under conditions that promote proliferation of the human HSCs for about 3 to about 10 days, whereby an expanded population comprising CD34+ human HSCs is obtained.

2. The method of claim 1, wherein the expanded population comprises at least 3-fold more CD34+ HSCs than the cell population of step (a).

3. The method of claim 1, further comprising obtaining the cell population of step (a) from a human subject.

4. The method of claim 1, wherein the cell population comprising the HSCs is derived from umbilical cord blood or bone marrow.

5. The method of claim 1, wherein the synthetic fetal liver organoid constitutes a coating on a solid carrier.

6. The method of claim 5, wherein the carrier is a particulate support.

7. The method of claim 1, further comprising administering the expanded population of CD34+ human HSCs to a subject from whom the original cell population comprising HSCs is obtained.

8. The method of claim 1, wherein the contacted organoid is cultured in a medium selected from IMDM medium and APEL medium.

9. The method of claim 8, wherein the culture medium is supplemented with one or more of Stem Cell Factor (SCF), FMS-like Tyrosine Kinase 3 Ligand (FLT3L), and Thrombopoietin (TPO).

10. The method of claim 1, wherein the synthetic fetal liver organoid is obtained by:

(i) introducing into human pluripotent stem cells (hPSCs) one or more vectors comprising an inducible transgene encoding GATA-binding protein 6 (GATA6);

(ii) inducing expression of the GATA6 transgene in the hPSCs;

(iii) culturing the induced hPSCs in the presence of a pluripotency supporting medium for about 5 days, whereby a cell population comprising at least 70% $CXCR4^+$ cells is obtained; and (iv) culturing the cell population of step (iii) in a basal cell culture medium for about 10 days, whereby a synthetic, vascularized fetal liver organoid comprising $CD34^+$ endothelial-like cells, $NES^+$ mesenchymal stem cell-like cells, $DES^+$ stellate-like cells, and $CEBP\alpha^+$ hepatocyte-like cells is obtained.

11. The method of claim 10, wherein the human pluripotent stem cells are human embryonic stem cells or human induced pluripotent stem cells.

12. The method of claim 1, wherein the synthetic fetal liver organoid exhibits one or more properties selected from (i) an interconnected vasculature; (ii) differentiated cells within the mature liver organoid mutually contact each other in three dimensions; and (iii) more than one layer of cells.

13. A method for ex vivo expansion of human hematopoietic stem cells (HSCs), the method comprising (a) contacting a cell population comprising the human HSCs to a synthetic fetal liver organoid comprising mesenchymal-like cells, CD34-expressing (CD34+)

endothelial-like cells, desmin-expressing (DES+) stellate-like cells, and CEBPα+ hepatocyte-like cells, wherein the synthetic fetal liver organoid is derived from embryonic stem cells (ESCs) or human pluripotent stem cells (hPSCs) engineered to express GATA6, wherein the cell population comprising the human HSCs are not derived from the engineered ESCs or hPSCs; and (b) culturing the contacted organoid under conditions that promote proliferation of the human HSCs for about 3 to about 10 days, whereby an expanded population comprising CD34+ human HSCs is obtained.

14. The method of claim 13, wherein before contacting the human HSCs with the fetal liver organoid, the method comprises isolating the human HSCs from a population of cells obtained from a tissue sample, umbilical cord blood, or bone marrow.

15. The method of claim 13, wherein the human HSCs are exogenous human HSCs.

\*    \*    \*    \*    \*